US008931379B2

(12) United States Patent
Allyn

(10) Patent No.: US 8,931,379 B2
(45) Date of Patent: Jan. 13, 2015

(54) METHODS AND DEVICES FOR SAFELY HANDLING A RAZOR BLADE

(71) Applicant: David L. Allyn, Clermont, FL (US)

(72) Inventor: David L. Allyn, Clermont, FL (US)

(*) Notice: Subject to any disclaimer, the term of this patent is extended or adjusted under 35 U.S.C. 154(b) by 251 days.

(21) Appl. No.: 13/653,687

(22) Filed: Oct. 17, 2012

(65) Prior Publication Data

US 2014/0107687 A1    Apr. 17, 2014

(51) Int. Cl.
*B26B 21/08*    (2006.01)

(52) U.S. Cl.
USPC .................................... 83/13; 30/51; 606/167

(58) Field of Classification Search
USPC ............... 30/50, 32, 51, 38, 39, 52; 606/167; 83/13
See application file for complete search history.

(56) References Cited

U.S. PATENT DOCUMENTS

| | | | | |
|---|---|---|---|---|
| 1,728,604 A | * | 9/1929 | Giglio | 30/333 |
| 1,860,454 A | * | 5/1932 | Dessell | 30/320 |
| 2,301,925 A | * | 11/1942 | Benjamin | 206/354 |
| 2,397,444 A | * | 3/1946 | Stern | 30/162 |
| 2,453,198 A | | 11/1948 | Corbett | |
| 2,599,439 A | * | 6/1952 | Drake | 30/151 |
| 2,613,438 A | * | 10/1952 | Robinson | 30/331 |
| 2,628,423 A | * | 2/1953 | Cuntz | 30/156 |
| 2,741,838 A | * | 4/1956 | Breazeale | 30/40.2 |
| 2,849,109 A | * | 8/1958 | Rommel | 206/352 |
| 3,078,572 A | * | 2/1963 | Everton | 30/333 |
| 3,088,252 A | * | 5/1963 | Schmidt | 451/378 |
| 3,337,100 A | * | 8/1967 | Berning | 224/182 |
| 3,407,496 A | * | 10/1968 | Pomper | 30/49 |
| 3,574,936 A | * | 4/1971 | Bullerman | 30/29.5 |
| 3,599,327 A | * | 8/1971 | Calandra | 30/30 |
| 3,667,122 A | * | 6/1972 | Black | 30/286 |
| 3,899,828 A | * | 8/1975 | Bosco | 30/151 |
| 4,037,322 A | | 7/1977 | Bresler | |
| 4,328,615 A | | 5/1982 | Bowman et al. | |
| 4,681,223 A | * | 7/1987 | Roberts | 206/354 |
| 4,712,300 A | * | 12/1987 | Hemmeter | 30/41 |
| 4,821,418 A | * | 4/1989 | Windhager | 30/329 |
| 4,916,816 A | * | 4/1990 | Richman | 30/339 |
| 4,942,662 A | * | 7/1990 | Radcliffe | 30/49 |
| 4,943,295 A | | 7/1990 | Hartlaub et al. | |
| 4,979,300 A | * | 12/1990 | Blank et al. | 30/169 |
| 5,048,184 A | * | 9/1991 | Saxton | 30/169 |
| 5,148,916 A | * | 9/1992 | Tillyer, Sr. | 206/352 |

(Continued)

OTHER PUBLICATIONS

Alguire, P.C. et al., "Skin Biopsy Techniques for the Internist," *J Gen Intern Med*, Jan. 1998, pp. 46-54, vol. 13, No. 1.

(Continued)

*Primary Examiner* — Sean Michalski
(74) *Attorney, Agent, or Firm* — Saliwanchik, Lloyd & Eisenschenk

(57) ABSTRACT

Biosafety blade devices that aid in the manipulation and safety of either single-edged or double-edged razor blades are disclosed. The devices include finger guards that assist with holding and manipulating a razor blade. The device also includes various embodiments of blade guards that prevent accidental contact with the sharp edge of a razor blade, securely lock a blade preventing reuse, minimize recoil and flying projectiles, control the depth of a skin biopsy, reversibly fix blade curvature and allow for tissue to be measured and securely held to the blade or easily expelled into a specimen container. The components of the biosafety blade, i.e., the finger guards and blade guards, can be used separately or they can be combined to provide for maximum comfort, accuracy, versatility and safety.

110 Claims, 11 Drawing Sheets

(56) References Cited

U.S. PATENT DOCUMENTS

| | | | |
|---|---|---|---|
| 5,220,728 A * | 6/1993 | Ueno et al. | 30/30 |
| 5,555,892 A | 9/1996 | Tipton | |
| 5,624,451 A | 4/1997 | Segal | |
| 5,628,759 A * | 5/1997 | McCool et al. | 606/167 |
| 5,666,732 A * | 9/1997 | Shea | 30/329 |
| 5,674,234 A | 10/1997 | McCool et al. | |
| 5,727,682 A | 3/1998 | Abidin et al. | |
| 5,979,056 A | 11/1999 | Andrews | |
| 6,505,403 B1 * | 1/2003 | Andrews | 30/29.5 |
| 6,550,141 B1 * | 4/2003 | Rivers et al. | 30/50 |
| 6,938,765 B2 * | 9/2005 | Awad | 206/354 |
| 7,337,903 B2 * | 3/2008 | Lauri | 206/350 |
| 7,930,830 B2 | 4/2011 | Gringer et al. | |
| 7,998,161 B2 | 8/2011 | Shi | |
| 2008/0065126 A1 | 3/2008 | Endo | |
| 2011/0130678 A1 | 6/2011 | Williamson, IV | |
| 2014/0182618 A1 * | 7/2014 | Jafari Dehnavi | 132/325 |

OTHER PUBLICATIONS http://www.miltex.com/prodinfo/surgical/biopblade.aspx, pp. 1-2.
http://www.delasco.com/pcat/1/Sharps/Personna_DermaBlade/dlmid034/, pp. 1-2.

* cited by examiner

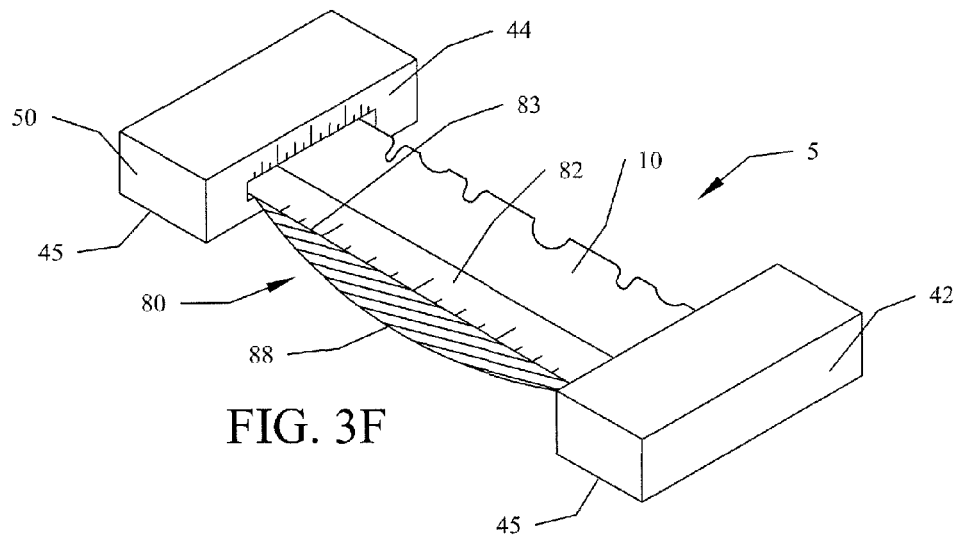
FIG. 3F
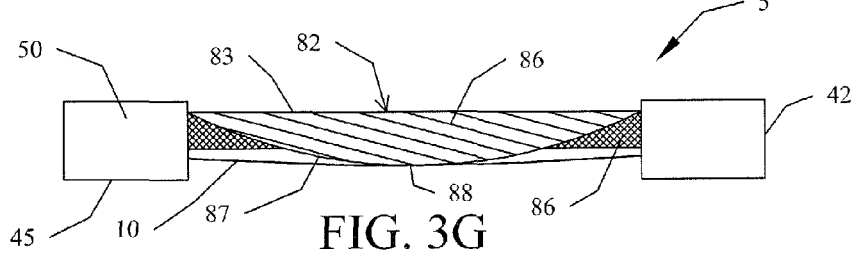
FIG. 3G
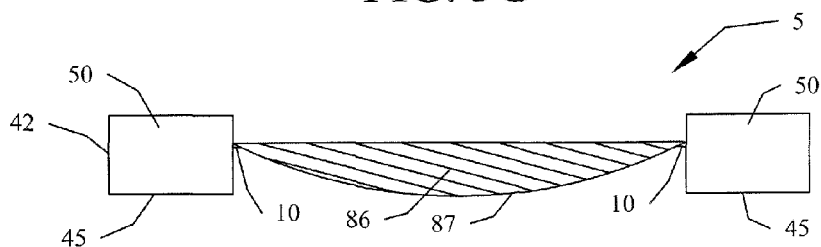
FIG. 3H
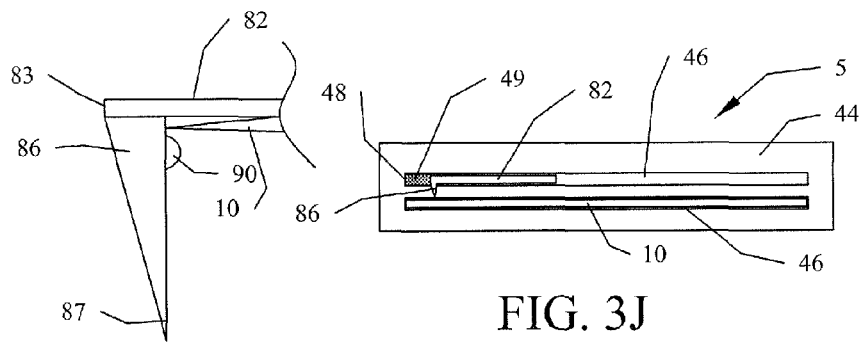
FIG. 3I
FIG. 3J

METHODS AND DEVICES FOR SAFELY HANDLING A RAZOR BLADE

BACKGROUND OF INVENTION

Dermatology is a broad field of medicine that specializes in the diagnosis and treatment of various skin conditions. Oftentimes, such diagnosis and/or treatment requires curettage or even the removal of a small portion of skin, perhaps for biopsy purposes or to eliminate an undesirable growth, such as a mole or wart. The method utilized to remove a skin sample will depend in part on the skin depth to which the sample must be taken.

The shave method is most commonly utilized when a skin sample will be confined to the epidermal and dermal layers. It is relatively simple to perform and requires only a sharp razor blade. Typically, a double-edge stainless steel razor blade, the type with a longitudinal spindle slot, is broken or "cracked" longitudinally along the length of the spindle slot. One half of the blade is then held between the thumb and either the forefinger or middle finger and used to gently shave off the desired amount of skin. If necessary, the blade can be squeezed or pressed between the two fingers to impart a bend to the blade for taking a sample slightly below the epidermis into the dermis (or less commonly subcutis/fat). Razor blades are ideal for this procedure because their flexibility allows a dermatologist or other medical practitioner considerable control over the size and depth of the sample taken. They are also inexpensive, the wounds tend to heal quickly, and they cause little or no obvious scarring.

While effective, razor blades can be dangerous to use. The sharp edges can be hazardous to manipulate and are difficult to pick up when dropped on a flat surface. Further, if a blade that is bent during use should slip out of the fingers, if can become a dangerous projectile. If a medical professional or patient becomes accidentally injured by the blade, there is a possibility of blood exposure and contamination.

Unfortunately, despite the frequency with which razor blades are used for various procedures, there has been little or no development of a convenient, safe way to hold a razor blade or to conceal the sharp edges when not in use. More particularly, there has been little advancement to ensure that razor blades do not become hazardous projectiles or, if they do, that the sharp edges are protected from accidental contact.

Thus, given that the use of razor blades will likely continue for medical procedures, it is imperative that there be a safe, convenient way to hold and manipulate a razor blade that does not compromise the blade flexibility. More particularly, there is a need for a device that can conceal, protect and secure one or more sharp edges of a razor blade when not in use or when not being securely held.

BRIEF SUMMARY

In accordance with the embodiments of the subject invention, the problem of comfortably and safely holding and manipulating a single or double-edge razor blade, or some part thereof, is solved by the use of one or more finger guards that can be attached to a single- or double-edge razor blade. In further accordance with embodiments of the subject invention, the problem of securing one or more sharp edges of the blade, so that they are prevented from causing accidental injury, is solved by the use of one or more blade guards. The finger guards and blade guards of the subject invention can be used separately. But, in certain embodiments, the finger guards and blade guards are used together. These, and other embodiments of the subject invention, successfully address the above described disadvantages associated with using razor blades in dermatology or other medical procedures and provide certain attributes and advantages, which have not been realized previously. In particular, the subject invention provides novel, inexpensive, and highly effective methods and devices for the convenient and safe use of razor blades for skin shaving sample procedures and other medical procedures. While the embodiments described herein can be limited to single use, it should be understood that the devices can be used multiple times before disposal. The embodiments herein can also comprise materials that permit sterilization, such that the devices can be reused.

When using a razor blade for a procedure, a medical professional must determine whether a whole razor blade is appropriate to use, or if the blade should be "cracked" in half, so that only one sharp edge is used. Typically, one half of a whole razor blade is used for dermatologic procedures and referred to as a "half-blade". Regardless of whether a whole or half-blade is utilized, it is important that it be held securely for accurate and safe manipulation during a procedure. Typically, in use, the blunt ends of the razor blade are held between two fingers and the curvature of the blade is adjusted by squeezing the two ends together. This method of holding and/or squeezing the blunt ends can be awkward and uncomfortable on the fingers.

One embodiment of the invention utilizes finger guards that can be affixed, either removably or permanently, to the blunt ends of a whole or half-blade. The finger guards can have grooves or slots into which the blunt ends of the blade can be inserted. In one embodiment, the finger guards have one, possibly more, surfaces, which can be broader than the blunt end of the blade, against which the fingers can be placed. A broader surface can be more comfortable to use and provide a better grip on the blade for more secure manipulation.

Another embodiment of the subject invention utilizes a blade guard to cover, conceal, or otherwise protect against one or more sharp edges of a blade. A blade guard can be incorporated with or otherwise utilized with one or more finger guards. In certain embodiments, a blade guard can be incorporated with a razor blade and without the use of finger guards. Thus, the embodiments herein can be used with blades having a single sharp edge or with a double-edged blade. If utilized with a double-edged blade, the components described herein can be duplicated to operate with both sharp edges independently or simultaneously.

Other aspects and further scope of applicability of the present invention will become apparent from the detailed description and figures which follow. It should be understood, however, that the detailed descriptions, while indicating preferred embodiments of the invention, are given by way of illustration only, since various changes and modifications within the spirit and scope of the invention will become apparent from such descriptions and figures.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIGS. 3A, 3B, 3C, 3D, 3E, 3F, 3G, 3H, 3I, 3J, and 3K illustrate embodiments of a biosafety blade, according to the subject invention, utilizing a tab piece attached to an elongated plate—both of which can be movable.

DETAILED DISCLOSURE

Figure 1:
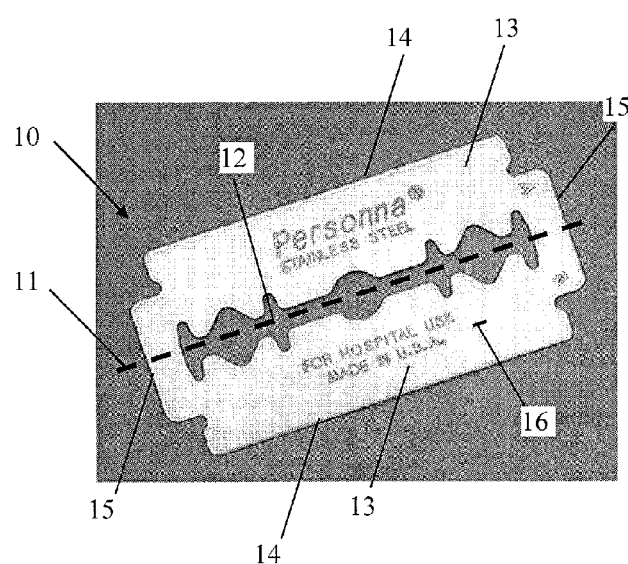
FIG. 1 shows a standard double-edge razor blade that can be utilized with the embodiments of the subject invention. Alternatively, a whole or half razor blade that can have similar dimensions, but different shapes, may also be utilized with embodiments of the subject invention.

The subject invention describes embodiments of methods and devices for holding and manipulating a razor blade and mechanisms to protect against the sharp edges of a razor blade. More specifically, the subject invention provides one or more embodiments of finger guards and blade guards, or similar devices, capable of providing a more comfortable and secure grip on a razor blade during use and ensuring against unintentional contact with one or more sharp edges. These devices when utilized separately or in combination provide a "biosafety blade" that is easier and safer to use.

The following description and figures will disclose that the subject invention is useful in the field of medicine, particularly in the field of dermatology, and more particularly with devices, such as razor blades, used for dermatological procedures such as curettage and the cutting and/or removal of skin. However, a person with skill in the art will be able to recognize numerous other uses that would be applicable to the devices and methods of the subject invention. While the subject application describes, and many of the terms herein relate to, a use for medical treatment, particularly of the skin, other modifications and uses apparent to a person with skill in the art and having benefit of the subject disclosure are contemplated to be within the scope of the present invention.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

For literary convenience, the term "finger" is used herein to refer to any of the fingers and the thumb. While specific reference is made herein to using the forefinger, middle finger, and the thumb to manipulate the embodiments of the subject invention, any of the fingers or thumb can be used. Thus, it should be understood that reference herein to "finger" can include the thumb, and any one or more of the fingers on a hand unless specifically stated otherwise.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

The various components described herein with a specific feature, structure, or characteristic related to a particular embodiment may be made of any material including but not limited to plastic, metal and metal alloy which is within the purview of one skilled in the art to affect such feature, structure, or characteristic of a particular component in connection with a related embodiment; and, various modifications and substitutions of the materials of any components can be effected without departing from the scope of the invention itself.

Reference will be made to the attached figures in which the same reference numerals are used throughout to indicate the same or similar components. With reference to the attached figures, which show certain embodiments of the subject invention, it can be seen that the subject invention pertains to finger guards 40 and blade guards 80, which can be utilized separately, or, in certain embodiments, can be combined and utilized together. A blade utilized with one or more embodiments of a finger guard and/or blade guard is referred to herein as a "biosafety blade." FIG. 1 illustrates an embodiment of a typical double-edge razor blade 10 that can be utilized with the embodiments of the subject invention. As shown in FIG. 1, a razor blade can have two sharp edges 14 and two blunt ends 15 and an upper blade surface 16. The dashed line 11 indicates where the razor blade is often "cracked" along the longitudinal spindle slot 12 to produce two half-blade 13 portions with one sharp edge 14 each and two blunt ends 15 on each side. The width (W) between the two sharp edges of a typical intact razor blade is approximately 2.0 cm and the length (L) between the blunt ends is approximately 4.3 cm. The embodiments of the subject invention can be utilized with an intact, whole razor blade or with a single half-blade portion. For literary convenience, and unless specified otherwise, the term "blade" as used herein refers to either an intact, whole razor blade or a half-blade. Alternative types of whole or half-blades may also be utilized with embodiments of the subject invention.

Figures 2A, 2B, 2C, 2D:
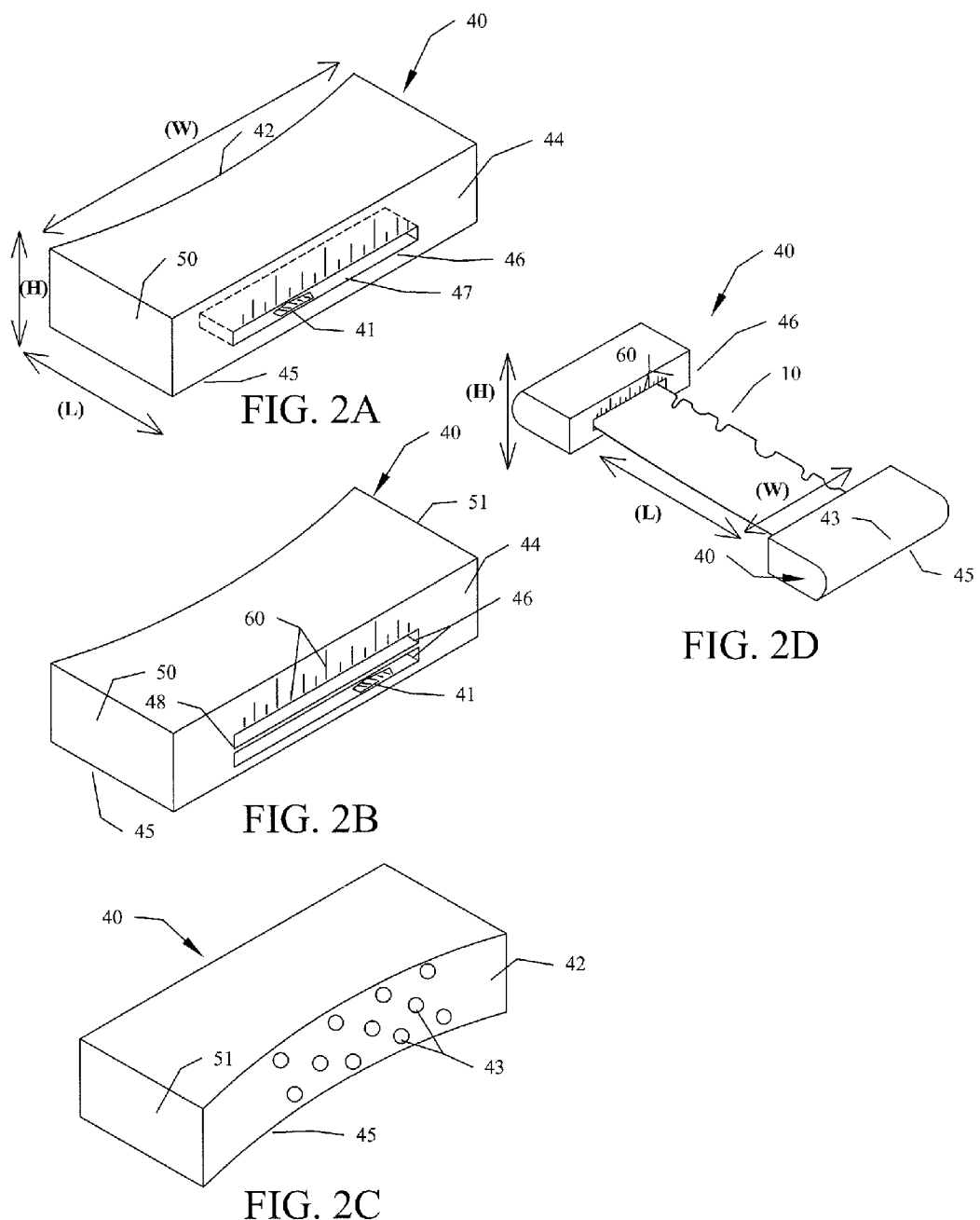
FIGS. 2A, 2B, 2C, and 2D illustrate embodiments of a finger guard and an example of how they can be attached to a "cracked" or half-blade (FIG. 2D). Note in FIG. 2A, the indication of length (L), width (W) and height (H) which is referred to throughout the description.

One embodiment of the invention comprises a finger guard 40 that can be placed over, pressed against, affixed to, or snapped the blunt end 15 of a blade. The overall shape of a finger guard can vary, but should, in general, have a shape that facilitates, or at least does not inhibit, the secure and accurate manipulation of a blade, particularly when force is applied to the blunt ends 15 of the blade or to the finger guard. The shape of the finger guard should also be such that it does not cause damage to the blade when used to apply force to the blunt ends of the blade. In one embodiment, the shape of the finger guard is such that it causes the blade and/or a blade guard associated therewith to preferentially bend in the desired direction when force is applied to the blunt ends of the blade/finger guard. FIGS. 2A, 2B, and 2C illustrate examples of a finger guard of the subject invention having an outside face 42 against which a finger can be placed. The outside face can have any of various ergonomic features or structures that facilitate secure placement of a finger. By way of non-limiting example, such as shown in FIG. 2C, the outside face can have some type of convex or concave curvature that conforms to, or is complimentary to, the shape of a finger. In a particular embodiment, the outside face has a width (W) between approximately 1.5 cm and approximately 2.5 cm and a height (H) of between approximately 0.4 cm. and approximately 1.2 cm. In a more specific embodiment, the outside face has a width of approximately 2.0 cm and a height of approximately 0.5 cm. The length (L) of a finger guard can also vary depending upon a variety of factors that would be understood by a person skilled in the art. In one embodiment, the length of a finger guard is between approximately 0.5 cm and 1.5 cm. In a more specific embodiment, the length of a finger guard is approximately 1 cm.

The outside face can also have any of a variety of gripping structures 43, such as, for example, ridges, bumps, raised shapes, depressions, or any other structure or configuration known to those with skill in the art, which aids in keeping a finger against the outside face during use. Alternatively, or in conjunction with the above described features, a gripping structure can be a rubberized, gel-like, elastomeric, or other type of shape-conforming material on the outside face, or other surfaces that facilitates gripping. In a specific embodiment, the finger guard is configured such that a blade attached thereto is in closer proximity to a bottom face 45 of the finger guard. This can promote bending of the blade in the direction of the bottom face 45, when the finger guards are squeezed together.

In a further embodiment, a finger guard has an inside face 44 that has one or more elongated openings or slots 46, an example of which is shown in FIGS. 2A and 2B. At least one slot can receive the blunt end 15 of a blade. The overall dimensions, such as (L) and (H) of the inside face can vary. In one embodiment, the dimensions of the inside face are the same as, or similar to, the dimensions of the outside face. Alternatively, the dimensions of the inside face are different than those of the outside face. As will be discussed below, additional slots within the inside face 44 of the finger guard can be used to secure other components. The depth (D) of a slot can vary, but, in general, at least one has a depth sufficient to receive and secure a blunt end of a blade. In one embodiment, the blade is inserted into a slot from the inside face 44 of the finger guard. In an alternative embodiment, a slot 46 extends through a finger guard, from the inside face to the outside face, such that a blade can be inserted into and through a slot from the outside face 42 to extend from the inside face 44 of the finger guard.

In one embodiment, the dimensions of the slot are such that one or more inside surfaces 47 of the slot provide a resistance fit with the blade, thus inhibiting it from being removed. Alternatively, there can be any of a variety of securing structures or apparatus 41 within or on the outside of the slot designed to secure a blade within the slot. Such devices or structures can provide, for example, a resistance fit to inhibit blade removal or they can, by way of additional example, utilize or interact with a blade's structure or shape to inhibit blade removal. In another alternative embodiment, the slot can have an adhesive or similar substance on one or more inside surfaces, so that when a blade is inserted, the adhesive contacts a blade surface, which inhibits the blade from being removed.

Since blades and plates are typically deformed into a curved configuration in use, it can be beneficial for a slot 46 to be able to accommodate changes in the shape of the blade. In one embodiment, a slot can have an interior shape, or have one or more inside surfaces that aids or, at least, does not prevent, bending of a blade or bowing of a blade guard, as will be described below. By way of non-limiting example, one or more inside surfaces can have an appropriate slant or be sufficiently flexible that it can accommodate the changing shape or orientation of a blade or blade guard when in use as described below. A person with skill in the art, having benefit of the subject application, would be able to determine any of a variety of structures or devices for securing a blade within a slot. Such alternatives are considered to be within the scope of the present invention.

The dimensions of a slot can vary depending upon whether a whole or half-blade will be utilized. In one embodiment, the length (L) of the slot is configured to accommodate either a half-blade or an intact whole blade. In an alternative embodiment, the length of the slot is more generic and can accommodate either type of blade. It can also be helpful, especially when obtaining a sample, to be able to determine if the size of the sample is sufficient, preferably with minimal or no unnecessary handling of the sample. In one embodiment, the inside face 44 has one or more measuring gradations 60. In a further embodiment, the gradations are positioned, so that the size of a sample on the blade can be determined with the gradations. FIGS. 2A-2C illustrate examples of gradations on a finger guard and FIG. 2D illustrates how a series of measuring gradations can be aligned relative to the blade, typically perpendicular to the sharp edge 14, so that measurements can be obtained.

In use, a finger guard can be affixed onto each side of a blade with the blunt ends securely within the slots, such as shown, for example, in FIG. 2D. A flat blade can be utilized for many dermatological procedures. However, for most uses, blades are typically more effective and accurate when curved. Thus, by applying force with the fingers to at least the outside faces 42 of the finger guards, the shape of the blade can be altered to impart a curve. If necessary, such curvature can cause the blade to extend past the finger guard, such as below the bottom face 45, making the sharp edge fully accessible for cutting. Depending upon the shape of a finger guard, more than one finger could be used to apply force against each side of the blade. For example, a finger guard could be configured with any of a variety of ergonomic features to accommodate more than one finger, such that perhaps two fingers could be used, with the opposing thumb to exert force on the blade. Advantageously, the use of finger guards can make the application of force more comfortable on the fingers than when applied directly to the blunt ends of a blade, which can improve accuracy and safety during use. The finger guard can also be ergonomically designed to allow for downward bending of the blade (and/or blade guard) when squeezed between the fingers. For example, the outside face could have a curvature that allows the finger guard to rotate on the fingers when squeezed. FIG. 2D illustrates an example of a finger guard with an outside face having a curvature that permits the finger guard to roll between the fingers causing the blade to bend downwards and the blade guard to bend downwards or upwards when an upright 92 (FIG. 4A) is utilized. This curvature of the finger guard controls not only the direction and bending of the blade but also the plate and/or tab of the blade guard.

In another embodiment, a slot for securing the blade can be located in closer proximity to, and generally parallel with, the bottom face 45 of a finger guard. This can ensure that when a finger guard is squeezed, the fingers will tend to roll the finger guards so that force is applied in a more downward direction, that is, towards the upper blade surface 16, causing the blade to bend towards the bottom face.

While the finger guards can provide some protection against accidental blade contact, the sharp edge is still exposed and presents a potential biohazard. The subject invention provides embodiments of a blade guard 80 that can conceal and protect the sharp edge of a blade to prevent accidental injury when not in use. Several of these blade guard embodiments can be used in conjunction with one or more of the above-described embodiments of finger guards. Other embodiments can be used without a finger guard. The combination of a blade with a blade guard 80 of the subject invention, with or without the use of finger guards, is referred to herein as a "biosafety blade" 5. A biosafety blade of the subject invention is convenient and easy to use and certain embodiments can comply with Occupational Safety and Health Administration (OSHA) and FDA Medical Device guidelines.

Figure 3A:
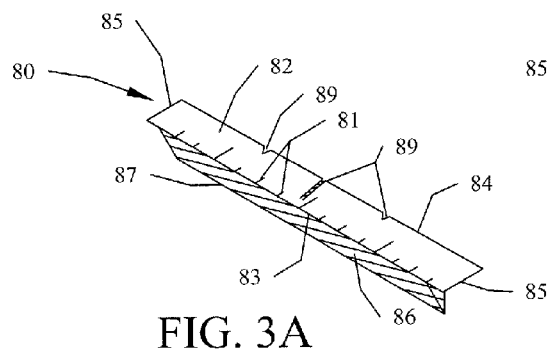
Figure 3C:
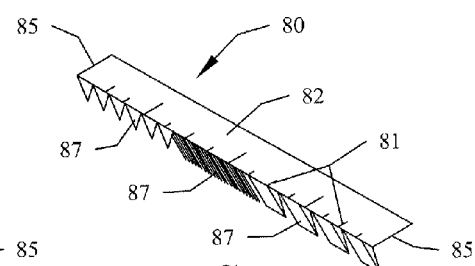
Figure 3B:
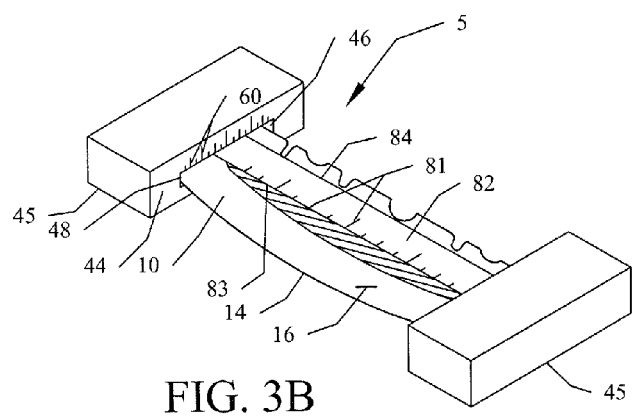

FIGS. 3A-3K illustrate one embodiment of a blade guard according to the subject invention. In this embodiment, a generally elongated, flat plate 82, as shown, for example, in FIGS. 3A and 3B, is positioned flat against the upper blade surface 16 and generally parallel to the blunt ends of a blade, as shown, for example, in FIG. 3B. In one embodiment, the width (W) of the plate, between the front edge 83 and the back edge 84, is narrower than the length (L) between the blunt ends. In a further embodiment, the plate can have a length (L) that permits the plate ends 85 to be positioned within a slot 46 of a finger guard, which can also be attached to the blunt ends of the blade, an example of which is shown in FIG. 3B. In one embodiment, the plate ends are positioned within the same slot as the blunt ends of the blade. In an alternative embodiment, the plate ends are positioned within a separate slot from that of the blade, as shown, for example, in FIG. 3E.

In one embodiment, the length (L) of the plate is approximately equivalent to the length of a razor blade. In a particular embodiment, the length of a plate is between approximately 4.0 cm and 4.5 cm and the width (W) is between approximately 0.3 cm and 0.5 cm. In a specific embodiment, the length of the plate is approximately 4.3 cm and the width of the plate is approximately 0.4 cm. Alternative embodiments may have one or more plates with different dimensions and configurations. In particular, a plate can have a length that is longer than the length of a blade or have a greater width. However, other embodiments may require a different width or plate configuration. Such variations in dimension and configuration are within the scope of the subject invention.

Figure 3E:
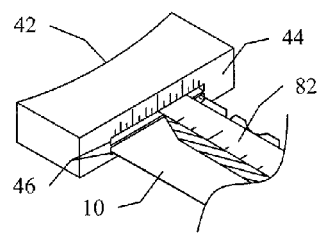

In one embodiment, the plate can slide either towards or away from the sharp edge of the blade, while being guided and/or aligned by the slots, as shown, for example, in FIGS. 3B and 3E. As described above, with regard to a blade, a plate can be similarly secured in a slot by any of a variety of techniques. For example, the dimensions of the slot can be such that one or more inside surfaces 47 of the slot provide a resistance fit with the plate, thus inhibiting it from being removed. Alternatively, there can also be any of a variety of structures within or on the outside of the slot designed to secure a plate within the slot. Such devices or structures can provide, for example, a resistance fit to inhibit plate removal or they may, by way of additional example, utilize or interact with a plate's structure or shape to inhibit blade removal. In another alternative embodiment, the slot can have an adhesive or similar substance on one or more inside surfaces, so that when a plate is inserted, the adhesive contacts a plate surface, which inhibits the plate from being removed.

Figure 3D:
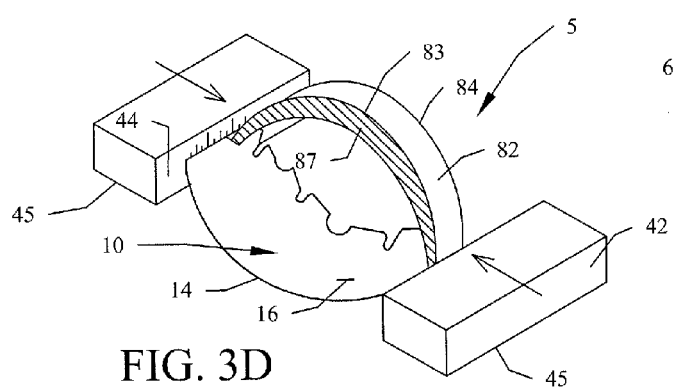
Figure 3K:
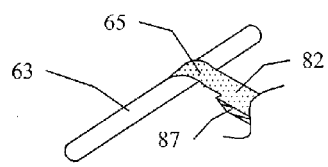

An alternative embodiment utilizes a rod 63 mounted securely within a slot 46. The plate ends can be operatively engaged with the rod, such as by having the plate ends curve around the rod or having one or more attachment flanges 65 that slidably couple with the rod. FIG. 3K illustrates an example of this embodiment. When the plate slides across the blade, rod and flanges keep the plate attached to the finger guard and guide the plate along the length of the slot. When the finger guards are squeezed, the plate 82 (and tab 86, which will be described below) can rotate, upward or downwards, while bending. In another alternative embodiment, a blade can also be operatively engaged with a rod in a slot, as described above. This can provide the blade with a similar downward rotation with bending.

Figure 7:
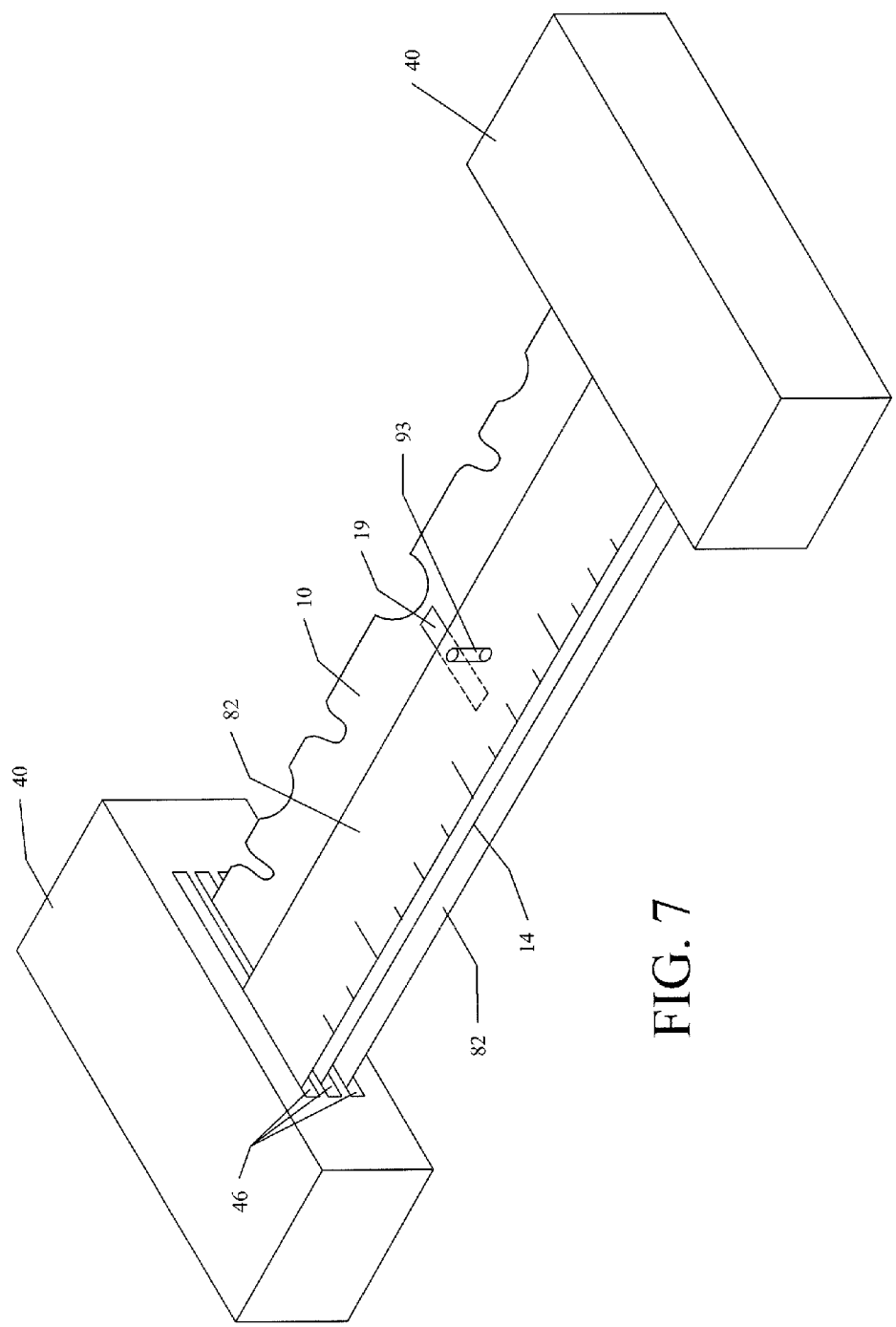
FIG. 7 illustrates an embodiment, of a biosafety blade according to the subject invention, having two operably connected plates above and below a blade.

While a single plate can prevent contact with the sharp edge of a blade from one side, it is possible for the sharp edge to make undesirable contact from the opposite, or unprotected, side. Therefore, it can be beneficial for a second plate 82 to be configured parallel to the first plate 82 on the opposite side of the blade from the first plate. Thus, with this embodiment, the sharp edge would be essentially sandwiched between two plates to better prevent any contact with the sharp edge. An example of this embodiment is shown in FIG. 7, where a first and a second plate are each positioned within separate slots 46 that are above and below the slot for the blade.

In a further embodiment, the first and second plates can be operably attached through a cut-out 19 within the blade. The cut-out can be an elongated opening that is generally perpendicular to the sharp edge, as seen in the example shown in FIG. 7. The operable connection between the first and second plates can be achieved by any of a variety of devices or techniques that provide at least one coupling 93, including, but not limited to, one or more pins, dowels, welds, adhesives, magnetic connections, or other devices or techniques known to those with skill in the art. When either of the plates is moved away from or towards the sharp edge, the coupling 93 between the two plates will ensure that both plates move simultaneously. FIG. 7 further illustrates an example of this embodiment In an alternative embodiment, the plate ends can be attached directly to the blade, an example of which is shown in FIG. 4B. In one embodiment, the plate ends 85 are inserted into or otherwise operatively connected to openings, such as, for example, grooves, ridges, tracks, or the like within or on the blade. In another embodiment, the plate ends are modified with one or more flanges 91 that are operably connected to one or more cut-outs, slits, notches, or other types of openings within the blade. In yet another embodiment, the one or more plates can have one or more coupling devices 93, such as, by way of example, one or more pins, dowels, runners, brackets, or the like, that are secured within and the grooves, ridges, tracks or other cut-outs 19 within the blade or the finger guard. FIG. 7 illustrates one example of this embodiment. With these embodiments, the blade guard can be configured to slide over the blade or it can be stationary.

Figure 8A:
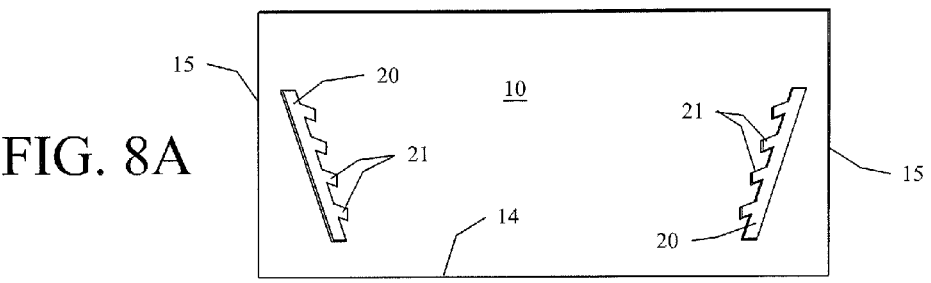
FIGS. 8A, 8B, 8C and 8D illustrate an embodiment of a biosafety blade, according to the subject invention, wherein a plate is operably connected to two oblique grooves, or cut-outs, within a blade. When the blade is flat, the plate covers the sharp edge. When the blunt ends of the blade are squeezed, the plate moves within the oblique grooves and slides away from the sharp edge. Similar oblique grooves, or cut-outs, may be placed inside a finger guard as well.
Figure 8B:
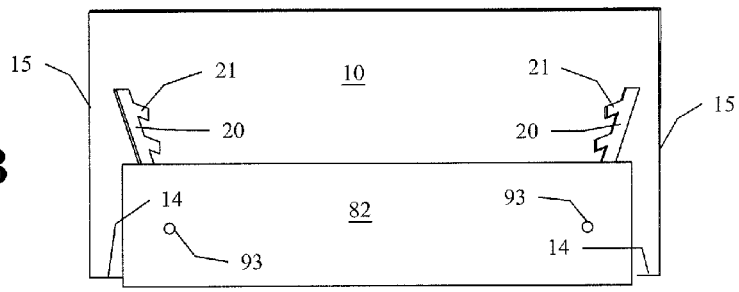
Figure 8C:
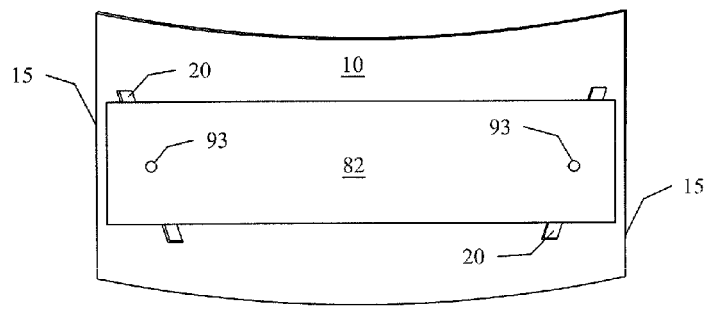

In one particular embodiment, the blade has two oblique cut-outs 20, such as shown, for example, in FIG. 8A. In one embodiment, the oblique cut-outs are angled so that their ends furthest from the sharp edge are closer to the blunt ends than the ends closest to the sharp edge. In other words, the oblique cut-outs form a "V" shape relative to the sharp edge. A plate can be secured to the blade by two or more coupling devices 93 that are slidably secured within the two oblique cut-outs, such as shown, for example, in FIGS. 8B-8C. These cut-outs may be made within the blade. When the blade is uncurved, the coupling devices 93 within the cut-outs 20 hold the plate over the sharp edge 14 of the blade, so that it actually covers the sharp edge. FIG. 8B shows an example of this. When the blunt ends 15 of the blade, with or without finger guards, are squeezed, the rigidity of the plate causes the oblique cut-outs to force the coupling devices 93 therein to move away from the sharp edge, which can simultaneously move the plate away from the sharp edge. An example of this is shown in FIG. 8C, where the curving of the blade moves the plate away from the sharp edge. When the blunt ends are no longer squeezed, the edges of the oblique cut-outs apply force against the coupling devices forcing them to move back towards the sharp edge, which, again, simultaneously moves the plate back over the sharp edge. Advantageously, this can prevent the sharp edge from being exposed if ever the blade is not properly secured between the fingers.

In an alternative embodiment, the blade can have two co-planar plates slidably secured within the two oblique cut-outs. In one embodiment, a second plate is secured to the one or more coupling devices 93 on the side of the blade opposite the first plate. This can present two plates in a parallel orientation with the blade essentially sandwiched between, as described above and shown, for example, in FIG. 7. As described above, the blunt ends 15 of the blade can be squeezed causing the rigidity of the plates acting with the coupling devices 93 to move against the oblique cut-outs, which forces the two attached plates to simultaneously move away from the sharp edge. When the blunt ends are no longer squeezed, the rigidity of the plates acting with the coupling devices again act against the oblique cut-outs 20 forcing the plates back over the sharp edge. Advantageously, this can prevent either side of the sharp edge from being exposed if ever the blade is not properly secured between the fingers.

Figure 8D:
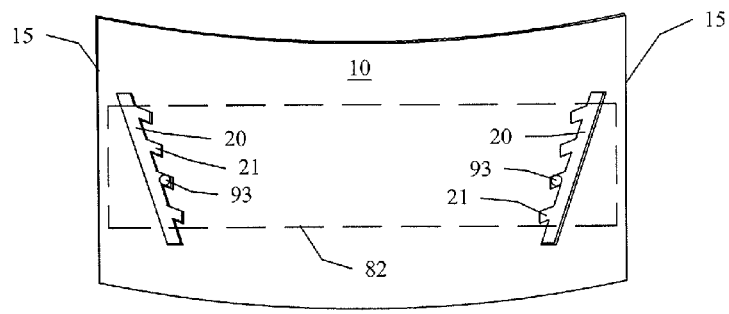

Additionally, the coupling device can be designed to act as a locking structure, similar to the embodiment shown in FIG. 3I. Alternatively, the ends of the plates can be crimped or have interdigitated ridges, so that they securely lock when the two plates are squeezed together. In a further embodiment, the oblique cut-outs can have one or more stops 21, which are additional cut-out sections along the path of, and contiguous with, the oblique cut-outs, an example of which is shown in FIGS. 8A and 8B. In one embodiment, the stops are angled relative to the oblique cut-out. In a further embodiment, the stops are located so that they are directed towards the center of the blade, i.e., away from the blunt ends. Alternatively, the stops can be directed towards the blunt ends or some combination thereof. By controlling the curvature of the blade, it is possible to align the one or more coupling devices 93 with one or more respective stops in an oblique cut-out. Releasing pressure on the blade, once they are aligned, causes the coupling devices to insert into the respective stops, holding the blade at that desired curvature. FIG. 8D shows an example of this wherein the coupling devices are shown positioned within two opposite stops within oblique cut-outs. To release the blade, the blunt ends 15 can again be squeezed, which forces the coupling devices out of the stops, and back into the oblique cut-out, where they can slide towards or away from the sharp edge depending upon the squeezing force.

In an alternative embodiment, the oblique cut-outs and/or stops may be modified and located within a finger guard and interact with a plate coupling device 97 to not only move the plate back and forth over the sharp edge of the blade, but also to hold the blade at a desired curvature. This is discussed in further detail below.

In still another embodiment, the plate ends or flanges thereon can be fixedly attached directly to the blade. FIG. 4B illustrates an example of a plate having flanges on the plate ends that are attached directly to a blade. In an alternative embodiment, the plate ends are clip-like devices that slide onto the sharp and/or dull ends of the blade and securely clip or attach the plate to the blade. Further alternative embodiments utilize a magnetic plate that can slide on the blade. Any of a variety of methods and devices, known to those with skill in the art, could be used to movably or immovably attach a plate of the subject invention to a blade. Such variations are considered to be within the scope of this invention. Attached at or about the front edge 83 of the plate there can be an elongate tab piece 86 that, like the plate, is positioned parallel to and between the blunt ends of the blade. The tab piece can be formed as part of or attached at or near the front edge by any of a variety devices and methods known to those with skill in the art. It can be attached directly to, or over, the front edge, or to the top or bottom surface of the blade, or some combination thereof. In a further embodiment, the tab piece comprises a fin 87 that completely, or at least partially, contacts the surface of the blade. The fin can be thinner or narrower than the rest of the tab piece, but it does not have to be. In one embodiment, all or most of the length of the tab piece terminates in a fin portion that contacts the blade. In a further embodiment, the fin 87 has a continuous edge in contact with the blade, so that all or most of the fin makes uniform contact with the blade, an example of which is shown in FIGS. 3A, 3C, 3G, 3H, and 3I. In an alternative embodiment, the fin portion has an edge in contact with the blade that is toothed, notched, bristled, or has some other discontinuous configuration, causing discontinuous contact with the blade, as shown by the examples in FIG. 3C. In a particular embodiment, the plate, with its ends secured within the slots or to the blade, can exert a force against the tab piece that aids in maintaining contact of the fin 87 with the upper surface 16 of the blade. It can be beneficial for the fin to have sufficient rigidity so that it does not collapse or deform detrimentally under the pressure applied by the plate.

Several factors can dictate the different dimensions and shape that a tab piece can have. In a particular embodiment, the tab piece is a generally triangular, wedge-shaped construction where one flat surface is fixedly attached to the plate and one sharp edge is in contact with the blade. One example of this is shown in FIG. 3I. In a specific embodiment, the height of the tab piece is between approximately 1.0 mm and approximately 2.0 mm and the edge that is fixedly attached to the plate has a width between approximately 0.1 cm and approximately 0.3 cm. More specifically, the height of the tab piece is approximately 1.5 mm and the width of the edge that is fixedly attached to the plate is approximately 1.0 mm.

To use a safety blade of the subject invention, the plate can be slid away from the sharp edge 14. The blunt ends, with or without finger guards, can be squeezed to create a curve in the blade. Ideally, as the blade 10 bends towards the bottom face 45 of the finger guards, the blade guard 80 can bow in the opposite direction. FIG. 3D illustrates an example of this configuration. The sharp edge 14 of the blade can then be used as desired. Once the sharp edge has been used, the pressure on the finger guards can be reduced, so that the blade is no longer curved and the blade guard straightens and again contacts the surface of the blade. At this point, if desired, gradations that can be on the plate and/or on the inside face 44 of the finger guard can be used to measure whatever sample, substance, or object is on the blade. In a further embodiment, the tab piece, fin, or finger guard have one or more measurement gradations 60 and 81 that can be used to determine the size of a sample on the blade, such as shown, for example, in FIGS. 3A, 3B and 3C. Such gradations can be lines, numbers, or other symbols or combinations thereof.

To remove whatever is on the blade, or to clean the blade, the blade guard can be slid, such as with a finger, towards the sharp edge of the blade, pushing or sliding whatever is on the blade towards, and off of, the sharp edge.

By way of a non-limiting example, the biosafety blade can be used to obtain a skin biopsy sample. By squeezing the finger guards to create a curve in the blade and cause the blade guard to bow in the opposite direction, the sharp edge, as well as the surface of the blade, is available for use. Once a skin sample is obtained, pressure on the finger guards can be released. The sample can then be measured with various gradations on the plate, tab, fin, and/or the finger guard(s). When desired, the blade guard can be pushed towards the sharp edge, so that the tab and/or fin can slide or push the sample towards the sharp edge of the blade, where it can, preferably, be dropped or placed into a prepared container or on a surface for later analysis. Further, when pressure is released and the plate is parallel to the blade, the plate can aid in holding a biopsy specimen onto the blade, by pressing it securely against the blade to prevent accidental falling and loss of the specimen and subsequent contamination.

When the finger guards are squeezed and the blade guard is positioned between the sharp edge 14 and opposite dull edge of the blade 10, it is possible for the blade guard components to bend in the same direction as the blade and not interfere with utilization of the sharp cutting edge 14 or blade upper surface 16. While this is not detrimental to using the blade, it may not be the preferred configuration. Alternatively, the blade 10 and blade guard 80 or plate 82 can bend in opposite directions when the finger guards and/or blunt blade ends 15 are squeezed together. An example of this is shown in FIG. 3D. In another embodiment, the fin can act as a biasing structure, exerting force between the blade and the plate. When the blunt ends of the blade are squeezed together, the fin can ensure that the blade and plate bend or curve in opposite directions. FIG. 3B shows an example of how a tab piece can impart a resting downward bend to the blade and upward bend to the plate, which helps to ensure proper opposite bending of the blade and blade guard when the finger guards and/or blade ends are squeezed. However, it can be beneficial to incorporate additional structural features to the blade and finger guards to ensure this reaction. A wide variety of methods and devices that can be useful for encouraging proper curving or bending of the embodiments of the subject invention will be apparent to a person with skill in the art. Substitution of other methods or devices, other than those specifically described herein, is deemed to be within the scope of the subject invention.

In one embodiment, the tab and/or the fin can have a semi-circular or approximately semi-circular shape, such as shown, for example, in FIGS. 3B and 3G. When force is applied to the blunt ends, with or without finger guards, the apex 88 of the semi-circle can maintain contact with the blade surface as the blade guard bends, which can urge the blade to curve in the opposite direction. In a further embodiment, the plate can exert a force against the tab piece that causes it and the fin to imbue the blade with a slight curve. This ever-present slight curvature can ensure that the blade continues to curve in the appropriate direction when additional force is applied to the blunt ends. Alternatively, one or more surfaces within the slots 46 can be configured at an angle, so that the blade and/or blade guard are maintained with a slight curvature. When the finger guards are squeezed, the desired bending of the blade and/or blade guard is achieved. In another alternative embodiment, the length of the plate can be shorter than that of the blade in the finger guards. The finger guards can be held in place by the shorter plate, which can be operably attached to slots, causing the blade to have a slight bend that can predetermine the direction of bend when the finger guards are squeezed. In a still further alternative embodiment, preferential tempering, notching or etching of the blade and/or plate ends 85 may cause desired bending in the upward or downward directions with squeezing of the finger guards.

In another embodiment, the blade guard has one or more cuts, cut-outs, notches, or similar features that create a guide 89, such as shown, for example, in FIG. 3A, to direct or encourage proper bowing of the blade guard when force is applied to the plate ends. In a further embodiment, the tab and/or fin has teeth, notches, or bristled areas, as described above, that encourage, or at least do not inhibit, bowing of the plate.

As mentioned above, one of the disadvantages of utilizing a blade is the constant exposure of the sharp edge. This is particularly problematic after a blade has been used and probably contaminated, since it then has the potential to become a biohazard. Thus, reducing or eliminating exposure of a used sharp edge can be of paramount importance. Advantageously, certain of the above-described embodiments of the blade guard can be employed to cover or conceal the sharp edge of a blade after it has been used and is the most dangerous.

In one embodiment, the blade guard can be pushed towards the sharp edge of a blade so that the tab piece goes over and covers the sharp edge 14. This may be the desired position for storage and transport of the biosafety blade prior to use. The blade guard may be retracted and upwardly bent away from the sharp blade edge by squeezing the finger guards as previously described. FIGS. 3F and 3H illustrate an example of this embodiment. As described above, the plate 82 and tab piece 86 can be configured to exert a force against the blade, which the rigidity of the blade naturally resists. This resistance force can provide the means by which the fin is kept in contact with the blade surface, as shown in the example in FIG. 3G. It has the further benefit of forcing the tab piece to go over the sharp edge when the blade guard is pushed fully towards the sharp edge, as shown in the example in FIG. 3H.

While a blade guard is beneficial in concealing a sharp edge, it can be important that the blade guard not be engaged over the sharp edge until necessary. Several methods can be employed to prevent the tab piece from being accidentally pushed over the sharp edge. In one embodiment, the slot can have a stop component 49 associated therewith that prevents one or both of the plate ends from abutting against a front inside surface 48 of a slot, an example of which is shown in FIG. 3J. A diversity of devices could be utilized as a stop or safety locking component for the subject invention. In one embodiment, a spring is mounted within the slot that biases the blade guard away from the sharp edge. When sufficient force is applied to the blade guard, the spring bias can be overcome to force the tab piece over the sharp edge. In another embodiment, an elastomeric material is placed at or near the front inside surface, such as, for example, a soft rubber or firm, gel-like substance. The resistance of the elastomeric material can provide an indication when the blade guard is near the sharp edge to prevent pushing the blade guard too far. But, when desired, the blade guard can be slid past the resistance of the elastomeric material, which can give way or be penetrated by the plate ends, allowing the tab piece to drop over the sharp edge. In a further embodiment, the slot can have a structure, such as, for example, a raised dimple that prevents the plate ends from abutting the front inside surface 48 of a slot. But, if sufficient force is applied to the tab piece, one or both of the plate ends can be forced over the dimple allowing the blade guard to move closer to the sharp edge and the tab piece to drop over and cover the sharp edge 14. It would be within the skill of a person trained in the art to devise any of a number of methods and devices that can control the operation of a blade guard according to the subject invention. Such variations are considered to be within the scope of the subject invention.

Once the tab piece 86 of the blade guard 80 covers the sharp edge 14 of the blade, it can be beneficial if the blade guard is difficult or impossible to remove, so as to maintain safety once the blade is secured and to prevent reuse of the blade. Ideally, the pressure exerted by the tab piece holds the tab piece over the sharp edge of the blade, which is shown in the example in FIGS. 3F and 3H. Further, the rigidity of the plate 82 can usually inhibit the blade guard from being forced back over the sharp edge. In fact, pressure applied on the plate in an attempt to remove the blade guard from the sharp edge can actually act to inhibit the tab piece from being forced back over and exposing the sharp edge.

To further prevent the possibility of the tab piece being forced away from the sharp edge, the tab piece can be designed to further engage with the sharp edge and prevent movement. In one embodiment, the tab piece can have one or more locking structures 90 that catch against or engage with the sharp edge. Similar locking structures of similar or different configurations may be part of, or attached to, the plate or located within the finger guards. Such structures can include, but are not limited to, one or more raised ridges or dimples, ribs, buttons, pawls, cut-outs, notches, grooves, ducts, swing-arm locks, or the like, that, in general, create a fixed fastening assembly between the sharp edge and the tab piece and lock the sharp edge into place. In a further embodiment, a slight pressure can be applied against the plate in order to force the sharp edge of the blade into a locking structure. FIG. 3I illustrates one embodiment of a locking structure that can be employed with the embodiments of the subject invention. In this embodiment, one or more raised dimples are located on the tab, directed towards the back edge 84 of the plate. When the tab piece goes over the sharp edge, the sharp edge moves towards the plate and the rigidity of the plate forces the sharp edge over the one or more dimples to secure the sharp edge between the plate and the dimple. If necessary, additional force can be applied to the plate to force the sharp edge over the one or more dimples.

Figure 4A:
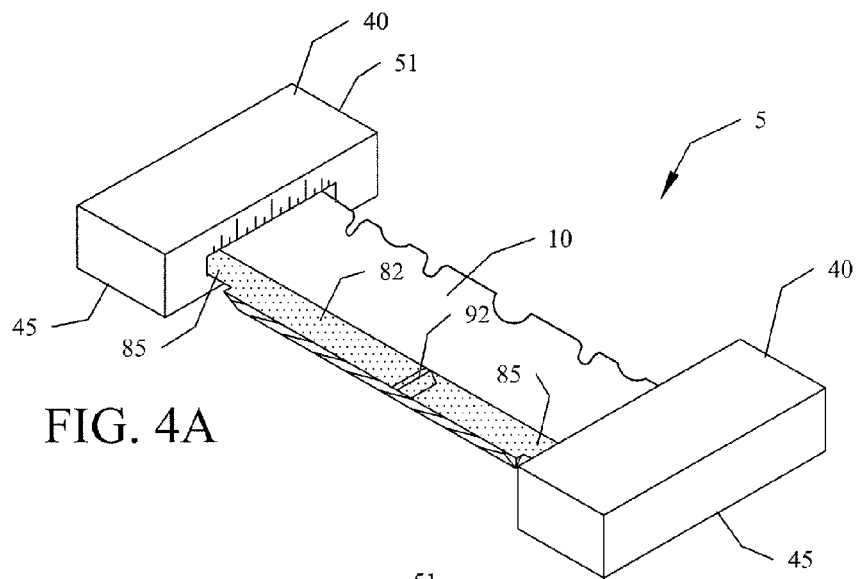
FIGS. 4A, 4B and 4C illustrate an alternative embodiment of a biosafety blade, according to the subject invention, utilizing a tab piece attached to an elongated plate. In this embodiment, the plate and tab piece are stationary, covering the sharp edge of the blade, but can bend when squeezed to expose the sharp edge.
Figure 4B:
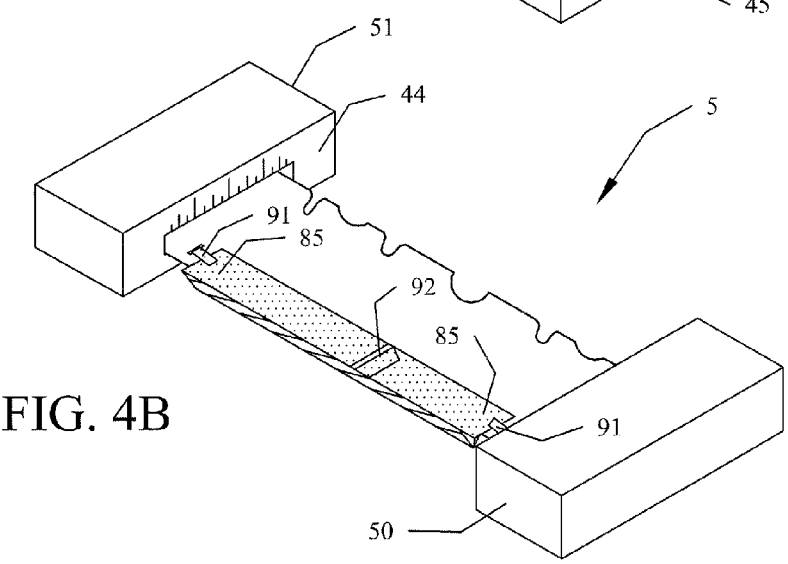
Figure 4C:
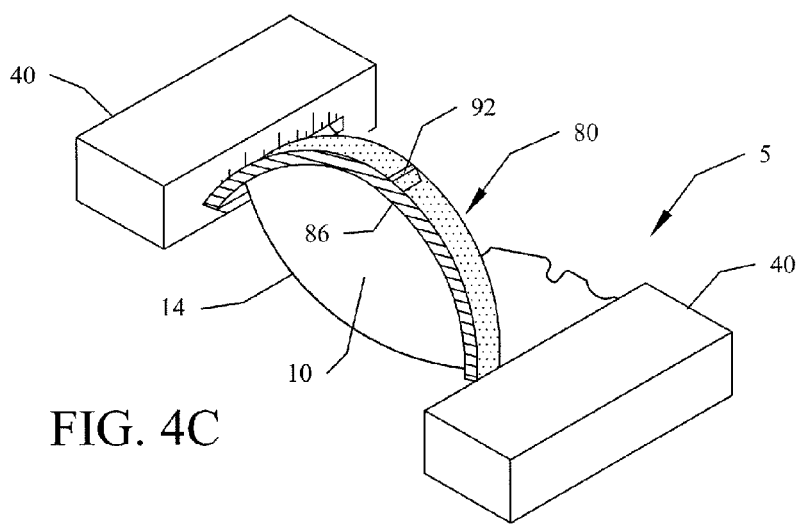

FIGS. 4A, 4B, and 4C illustrate yet another alternative embodiment wherein the blade guard 80 is configured to be permanently located at the sharp edge 14 of a blade, with the tab piece 86 protecting the sharp edge 14. In this embodiment, the plate ends 85 are fixedly attached to one or more finger guards 40 in such fashion that the blade guard does not move and the tab piece is over and covering the sharp edge. In one embodiment the plate ends are fixedly attached within a slot 46. FIG. 4A illustrates one example of this embodiment. The plate ends can be either in the same slot that the blade fits into, or they can be in a separate slot. In an alternative embodiment, the plate ends can be fixedly attached to the blade itself, which has been described above, and is shown, for example, in FIG. 4B.

With this embodiment, pressure applied to the blunt ends 15 of the blade can cause the blade to bend towards the bottom face 45 of the finger guards and the blade guard to bow in the opposite direction, similar to the process described above. Since the tab piece, in this embodiment, is designed to remain over the sharp edge when the biosafety blade 5 is not in use, it may not be necessary for the tab piece to have locking structures 90. However, locking structures may be desired to discourage re-use of a blade. In a further embodiment, the tab piece is configured to move or slide easily over or past the sharp edge when the plate bows.

In another embodiment, the plate or tab can have guides 89 to direct the bowing of the blade guard. For example, correct bowing may be achieved by etching, tempering, or notching the ends or edges of the blade guard or changing the blade guard's curvature, such as by angling the point of insertion within the finger guard, or by differing lengths of the blade and the blade guard, as described above.

In a further embodiment, an upright 92 is attached to the approximate center of the plate and contacts the blade. Since the blade and plate, in this embodiment, are substantially parallel, or in the same plane, such that they are substantially flat against each other, it is possible that when pressure is applied to the blunt ends of the blade, the blade guard could bend in the same direction as the blade. To prevent this, the upright 92 can push against the blade, causing a similar configuration as described above with the tab piece, where the blade and the blade guard are imparted with a slight bend in the appropriate and opposite direction. Thus, when pressure is applied to the blunt ends 15, or finger guards, the upright can ensure that the blade curves in one direction and the blade guard bows in the opposite direction. Notwithstanding, an alternative embodiment has the blade guard bending downward in the same direction and on top of the blade when the tab 86 is not engaged over the sharp edge 14 of the blade and the upright 92 may also be eliminated. This presents the sharp edge and the surface of the blade for use, as shown, for example, in FIG. 4C. Advantageously, with this embodiment, the sharp edge is always covered, unless the biosafety blade is being properly held and pressure applied to the blunt ends. Thus, should the biosafety blade slip out of the fingers and become a projectile, the sharp edge will be immediately covered, reducing the likelihood of it causing harm.

Figure 5A:
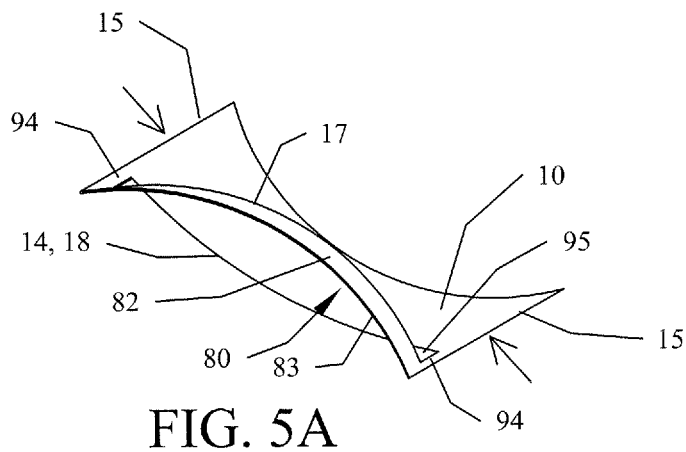
FIGS. 5A, 5B, and 5C illustrate an alternative embodiment of a biosafety blade, according to the subject invention, wherein a razor blade is modified with a plate that is longitudinally parallel with the sharp edge of the blade to restrict contact.
Figure 5B:
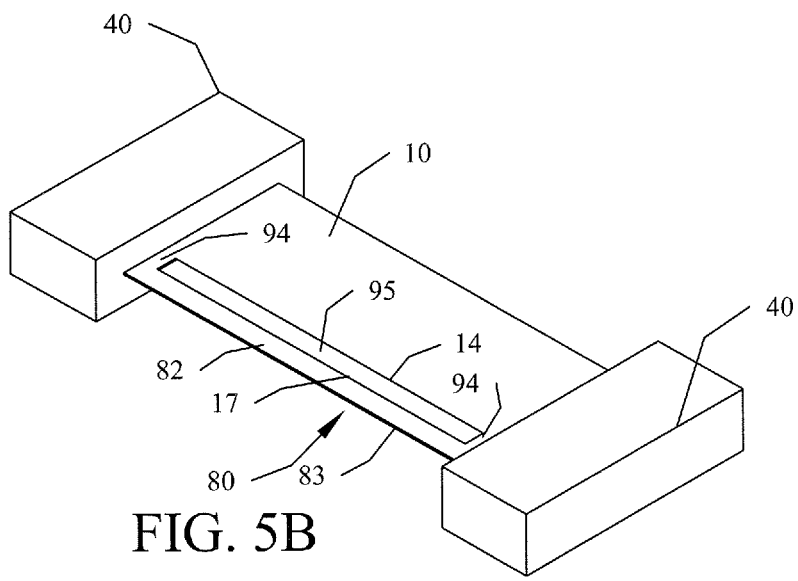
Figure 5C:
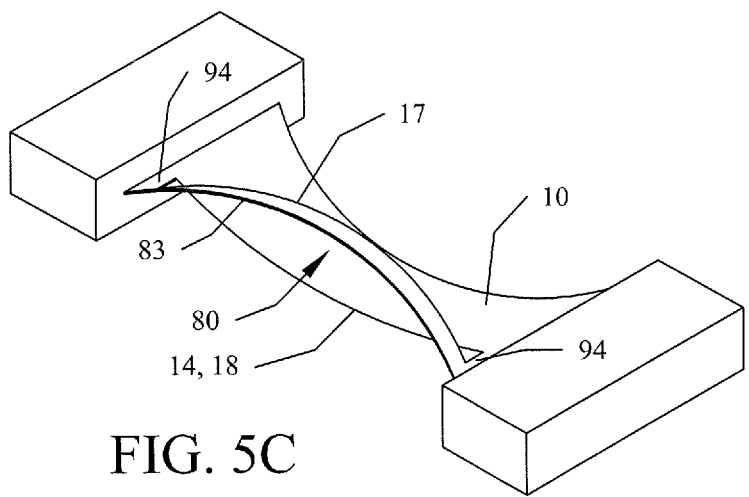

FIGS. 5A, 5B and 5C illustrate an alternative embodiment, wherein a plate 82 of the subject invention is manufactured, attached, or otherwise incorporated as a part of a blade. As seen in the example in FIG. 5A, a plate 82 can be incorporated with a blade by attachment of the blunt ends 15 to the plate ends 85. In one embodiment, this attachment is facilitated by use of one or more extensions 94. The extensions can attach at, or about, the blunt ends of the blade and at, or about, the plate ends, as shown in the examples in FIGS. 5A-C. In one embodiment, the plate is held in a longitudinally parallel orientation with the sharp edge of the blade. With this embodiment, the plate acts as a blade guard 80 inhibiting contact with the sharp edge. In one embodiment the plate abuts the sharp edge, such that there is little or no space between the sharp edge and the plate. The plate may be straight, as shown in FIG. 5A, or the front edge 83 of the plate may be rounded or of various configurations. In an alternative embodiment, there is at least a small gap 95 between the plate and the sharp edge, as shown in the examples in FIGS. 5A, 5B, and 5C. The gap can be beneficial in preventing contact between the sharp edge and the plate, which can damage or dull the sharp edge.

Advantageously, the combined plate and blade embodiment can be amenable to the blade manufacturing process by creating a plate and a blade from the same piece of material. This can allow the combined plate and blade embodiment to be formed as a single unit rather than separately attached pieces. With this embodiment, a longitudinal gap 95 between the blunt ends can be created within a side of the blade material where a sharp edge is desired. This can create a front edge 17 and a rear edge 18 and two extensions 94 that are substantially perpendicular to the blunt ends 15. An example of this can be seen in FIG. 5B. The rear edge 18 can be utilized as the sharp edge and the front edge 17 can define one boundary of the plate 82. In an alternative embodiment, a protective bi-directional tab piece may be attached to the front edge 17 as an additional safety feature.

With either of these embodiments, where the blade and the blade guard are combined, one or more finger guards 40 can be used on the blunt ends. In use, when pressure is applied to the blunt ends, the blade 10 will tend to curve downwards and the blade guard will tend to bow upwards. Several devices and techniques, which are known to, or which could be devised by, those with skill in the art, could also be employed to ensure that the blade and blade guard bend in opposite directions. By way of non-limiting example, the extensions 94 could be modified in such a way as to direct the movements of the blade and blade guard, but not reduce the effectiveness of the blade guard from preventing undesirable contact with the sharp edge. By way of further example, the gap could be created in such a manner that the blade and blade guard are urged to bend in the proper directions. Variations other than those described could be utilized and are considered to be within the scope of the subject invention.

Figure 6A:
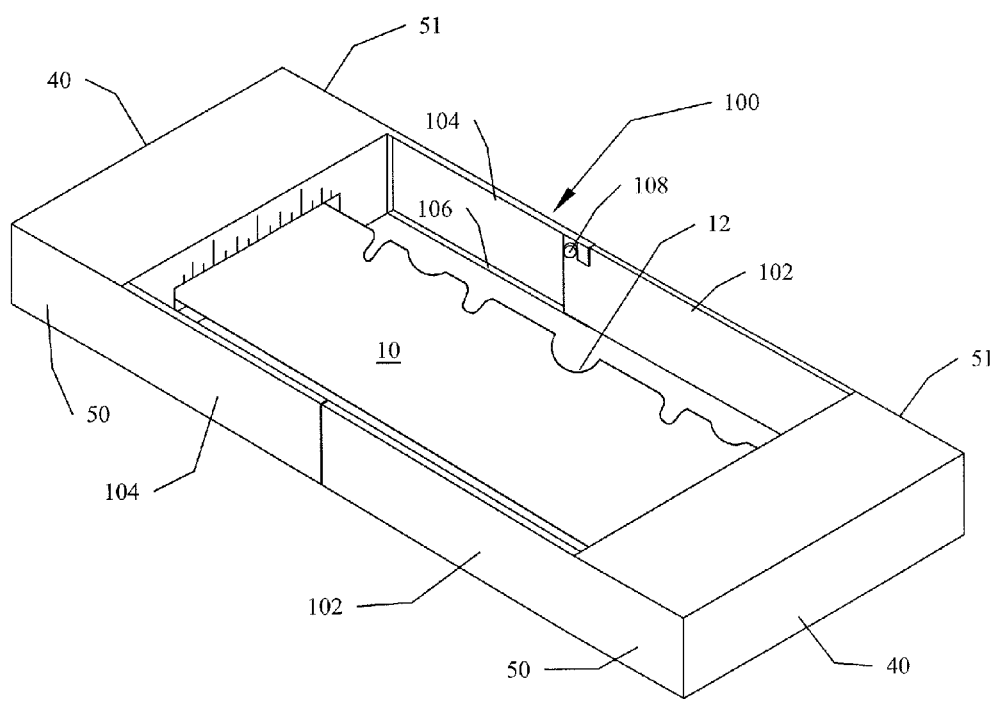
FIGS. 6A and 6B illustrate an embodiment of a biosafety blade, according to the subject invention, wherein a receiver and an arm are slidably attached along each length (L) of a blade to form a frame around the blade to protect the sharp edge against contact and allow bending of the blade.

Another embodiment of the subject invention utilizes a modified combination of some of the features described previously. FIG. 6A illustrates an embodiment of a blade that is substantially surrounded by a frame 100, which incorporates at least two finger guards 40. In this embodiment, the blunt ends of the blade are held within at least two finger guards, or an equivalent type of structure, similar to the embodiment shown in FIG. 2D. The finger guards can have a leading face 50 and a following face 51. In a further embodiment, extending from the leading face of one finger guard is an arm 102 and extending from the leading face of another finger guard is a receiver 104. The arm and the receiver can extend parallel to the length of the sharp edge 14, as shown, for example, in FIG. 6A.

In a further embodiment, an arm extends from a following face 51 of one finger guard and a receiver extends from a following face 51 of another finger guard. Thus, in this embodiment, there are two arms and two receivers extending from the finger guards to form a complete frame around a blade. An example of this is shown in FIG. 6A. The arms and receivers can extend from the same finger guard or they can be alternated, so that one finger guard has both an arm and a receiver extending from it.

In a further embodiment, the arm and the receiver are cooperatively engaged so that when the finger guards are squeezed or pressure applied, the length of the arm and the receiver can be compressed, reduced, or otherwise altered, so that the finger guards can be brought closer together, and the frame can be compressed. This can cause the blade to curve towards the bottom face 45 of the finger guards. This frame compression can be achieved by the arm and the receiver sliding past one another, or one component can slide into the other. Alternatively, one or both components can be flexible or elastic or otherwise deformable. Configurations other than those listed, or modifications thereof, could also be utilized and a person with skill in the art would be able to devise any of a variety of such configuration and/or modification. Such alternatives are considered to be within the scope of the subject invention.

Figure 6B:
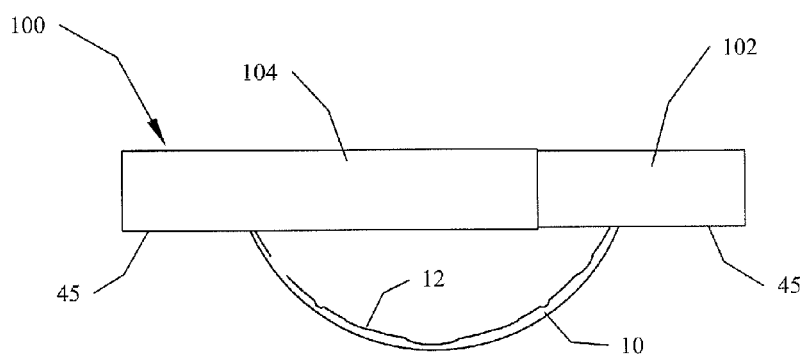

In a specific embodiment, the receiver 104 has at least one track 106 that receives the arm 102. The arm can have a complimentary structure that cooperates with the track, but this is not required. FIG. 6A illustrates an example of this embodiment. When the finger guards are squeezed, the arm slides along the track in the receiver decreasing the distance between the finger guards. This, in turn, can cause the blade to curve towards the bottom face 45 of the finger guards, making the sharp edge accessible for use. FIG. 6B illustrates an example of this embodiment.

In a further embodiment, the arm and/or the receiver can be biased so that in the absence of pressure on the finger guards, the arm and the receiver are maintained at their maximum distance. This embodiment can ensure that, when not in use, the sharp edge of the blade is uncurved and that the frame, particularly the arm and the receiver, block and minimize direct contact therewith. Ideally, the tension of the blade can act as a biasing element causing the finger guards to maintain maximum distance apart in the absence of force being applied to them. An advantage of this embodiment is that if the blade is released from the fingers during use, the lack of force on the finger guards will cause the blade to automatically straighten, pushing the finger guards apart, and the arm and the receiver to cover the sharp edge. This can prevent the uncontrolled blade from becoming a dangerous projectile and possibly a biohazard. In a further embodiment, one or more biasing structures, such as, for example, springs are incorporated into the frame to bias the arm.

In a further embodiment, one or more stops 108 are incorporated into the frame to prevent the arm and receiver from separating entirely. This can include one or more structures on the arm and/or the receiver that can ensure that they remain cooperatively engaged. In one embodiment the arm has a first ridge or dimple and the receiver has a similar second ridge or dimple. When the arm and receiver are fully biased, with the finger guards at maximum distance, the first dimple and the second dimple abut against each other inhibiting the arm and receiver from sliding fully apart. It would be well within the skill of a person trained in the art to create alternative devices and methods for maintaining the arm and the receiver in cooperative engagement. Such variations are within the scope of the present invention.

Figure 9A:
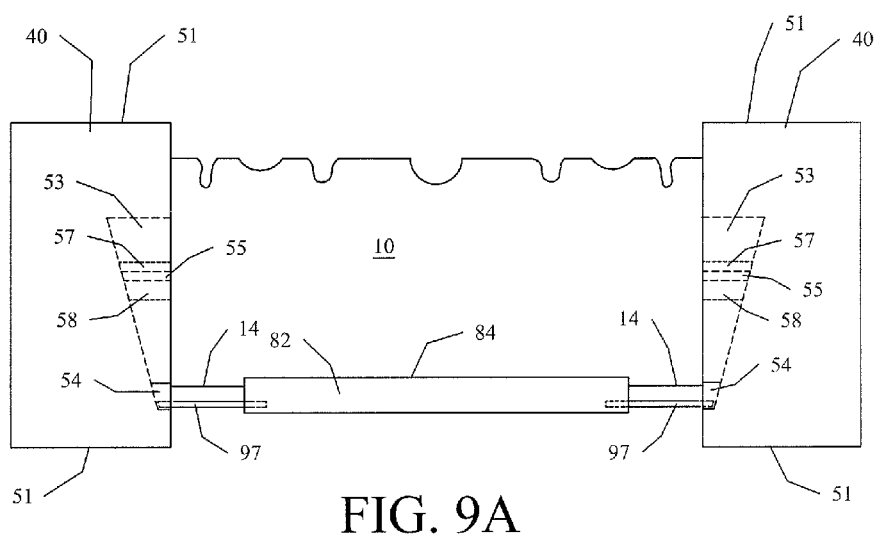
FIGS. 9A and 9B illustrate an embodiment of the subject invention, wherein the plate can be perpendicular to the sharp edge of a blade and is slidably connected to at least one (or more) drop slot(s) that is contiguous with at least one oblique slot within a finger guard. The plate can be rotated over the sharp edge of the blade by manipulation with one or more fingers or by squeezing the finger guards. Once the plate is rotated, the finger guards can be squeezed, which causes the plate to slide within the oblique slots and move away from the sharp edge.

Another embodiment incorporates several of the features and embodiments discussed above into a unique biosafety blade device. In this embodiment, a blade is secured between two finger guards 40, as described above, with each having a leading face 50 and a following face 51. In a further embodiment, there is a plate 82 positioned parallel with the blade and overlapping the sharp edge of the blade, similar to the example shown in FIGS. 7 and 8B. The ends of the plate can be operably engaged within an oblique slot 53. In one embodiment, an oblique slot 53 is similar to a slot 46 as described above, except that, in this embodiment, the oblique slot 53 increases in depth towards the following face 51. FIG. 9A illustrates one example of this embodiment. This embodiment operates similarly to the embodiments described above that utilize an oblique cut-out 20. Thus, in this embodiment, when the finger guards are squeezed together, the ends of the plate 82 that are operably engaged within the oblique slots 53 are forced towards the following face 51, which moves the plate away from the sharp edge. Likewise, when pressure is released on the finger guards, the oblique slot causes the operably engaged ends of the plate to move towards the leading face 50 so that the plate overlaps the sharp edge.

Figure 9B:
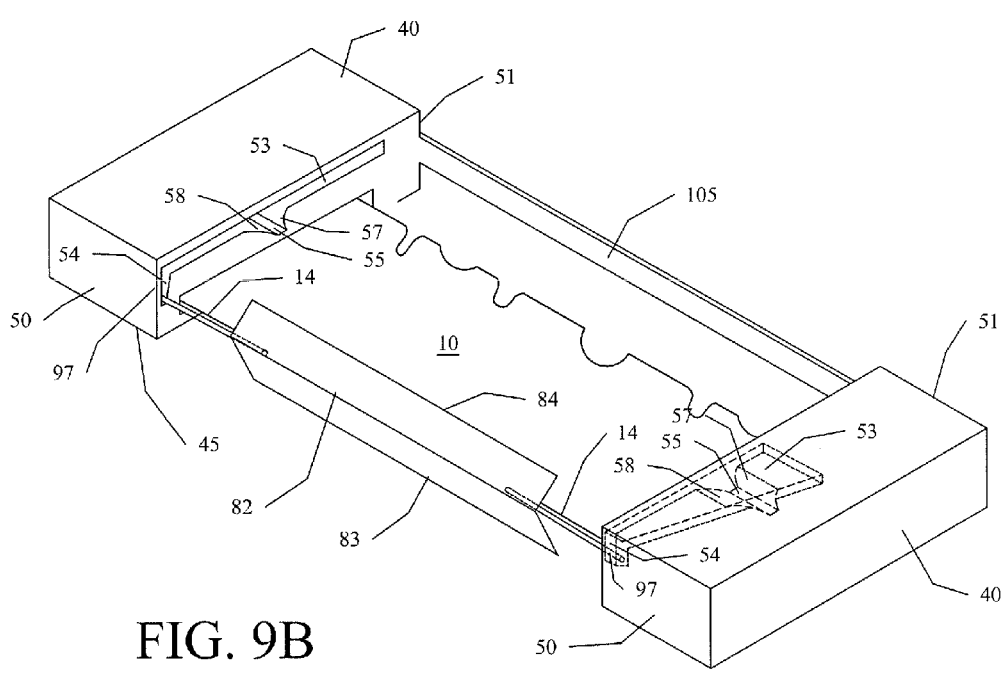

The ends of the plate or sliding mechanism 97 can be operably engaged with the oblique or drop slot 53 and 54 by any of a variety of configurations, devices, or techniques. In the simplest arrangement, the ends of the plate are configured as sliding mechanisms 97 or shaped to fit within and cooperate with the oblique slot. Alternatively, one or more sliding mechanisms 97, such as, for example, a pin, dowel, rod, arm, or similar devices, can be fixedly attached to the ends of the plate, so that they cooperatively engage the plate with the oblique or drop slots. FIG. 9B illustrates an example of this embodiment. In a further embodiment, the sliding mechanism 97 comprises a material or substance that aids in the movement of the sliding mechanism within the oblique or drop slots. Alternatively, the finger guard and/or the oblique or drop slots can comprise a material that aids in the movement of the ends of the plate or the sliding mechanism. In one embodiment, at least the ends of the plate or the sliding mechanism comprise a non-friction or non-sticking surface, such as, for example, a polytetrafluoroethylene (PTFE), such as, for example TEFLON, coated plastic or nylon material that creates minimal friction with the material of the finger guard and/or the oblique or drop slot.

In an alternative embodiment, the ends of the plate or sliding mechanism 97 may simply rotate and/or slide within a slot of various depths and/or configurations within the finger guards, without utilizing drop or oblique slots. In one embodiment, the ends of the plate or sliding mechanism can be tubular or otherwise rounded, so they can rotate against the inner surface of the slot of the finger guard. When the finger guards are pressed, the sliding mechanism will rotate causing the perpendicular plate to also rotate and become parallel with the blade, exposing the sharp edge 14. The parallel plate being above and in front of the sharp edge 14 of the blade can act to control the depth and amount of tissue collected. Further squeezing of the finger guards can cause the blade and plate to bend in opposite directions, as shown by way of example in FIG. 4C.

In an alternative embodiment, a slot 46 may be connected to and continuous with an oblique slot 53. As the finger guards are squeezed, the plate, protecting the sharp edge 14, can rotate as described above, from a position approximately perpendicular to the blade to being parallel with the blade, and then move along the oblique slot towards the following face 51 of the finger guard. In another embodiment, the rotation and movement of the plate in the oblique slot is allowed only wherein projections on the sliding mechanism 97 and within the oblique slot cooperatively engage as the finger guards are compressed resulting in rotation of the plate as it moves towards the following face 51. In still another embodiment, the movement of the sliding mechanism within the oblique slot can cause the vertically aligned plate to bump against or otherwise contact the blade causing the plate ends or the sliding mechanism to roll or rotate within a slot, causing the plate to become parallel to the blade and exposing the sharp edge. Other mechanical, spring, gear or magnetic configurations and/or devices may be similarly employed to ensure rotation and/or movement of the plate within the finger guards as they are compressed. It is within the skill of a person trained in the art to determine any of a variety of devices and methods for causing a plate to rotate relative to a blade. It is understood that such variations are within the scope of the subject invention.

While having the plate overlap the sharp edge is advantageous, there is always the possibility that undesirable or dangerous contact can still be made with the sharp edge. In a further embodiment, the oblique slot 53 comprises a drop slot 54 at the end nearest the leading face 50, an example of which is shown in FIGS. 9A and 9B. The drop slot can be a continuation of the oblique slot. The drop slot angles towards the bottom face 45 to form a receptical for the sliding mechanism. In a further embodiment, the drop slot is narrower at the end nearest the bottom face and widens where it is contiguous with the oblique slot, which is shown, for example, in FIG. 9A. In one embodiment, when the sliding mechanisms are positioned within the drop slots, the plate becomes positioned in front of the sharp edge of the blade. Because the shape of the drop slot is contiguous with the shape of the oblique slot, when the finger guards are squeezed, the sliding mechanisms are forced out of the drop slot and into the oblique slot, wherein continued pressure on the finger guards will move the sliding mechanisms, and the plate, away from the sharp edge.

In a further embodiment, the location of the blade relative to the drop slot can cause the blade to abut against the plate and temporarily interfere with the motion of the plate. Such abutment and interference can cause the plate to rotate, when the blunt ends of the blade are squeezed together, so that the plate moves over the blade and becomes generally or almost parallel to the sharp edge of the blade, such as shown, by way of example, in FIG. 9B. When the blunt ends continue to be squeezed, the blade can bend as described above. In one embodiment, the plate is generally flat. In an alternative embodiment, the plate can have a longitudinal bend or curve, such as, for example, a "V"-shape or be curved in a semicircle "C"-shape, so that when it is in front of the sharp edge, the front edge 83 and the back edge 84 of the plate extend over and better conceal the sharp edge. The bent "V" and curved "C" blade guard designs can also facilitate the upward bending of the blade guard with squeezing of the finger guards. FIGS. 9A and 9B illustrate this embodiment. Advantageously, with this embodiment, when the plate is in front of the sharp edge, the bend or curve can better prevent contact with the sharp edge.

In an alternative embodiment, when the sliding mechanism 97 is positioned within the drop slot (or the adjoining end of a slot or oblique slot), the plate becomes perpendicularly positioned in front of, and protects, the sharp edge of the blade. Because the drop slot is contiguous with the straight slot, which runs along the inside face 44 and lies perpendicular to the leading face 50 and following face 51 of the finger guard (FIG. 9B), one or more fingers can be used to manually rotate and/or move the plate over the sharp blade edge 14 and across the blade surface as the sliding mechanism moves along the drop slot and/or contiguous straight slot. In a further embodiment, a mechanical configuration can be employed to ensure manual rotation and/or movement of the plate within the drop and straight slots as the plate is moved with one or more fingers. By way of non-limiting example, one or more springs, gears, magnets, or other devices to encourage movement of the plate can be used. Alternatively, one or more sliding mechanism 97, such as a pin, dowel, pivot, arm, or similar devices can be fixedly attached to the ends of the plate to ensure cooperative engagement of the plate with the drop and/or straight slots. Alternatively, the ends of the plate itself can have various notches, ridges or other shapes and/or configurations that can cooperatively engage the plate with a slot. In addition, the one or more slots, drop slots, or oblique slots can be continuous slots, grooves or tracts with various directions, shapes and configurations; or, slots and grooves with notches, bumps, ridges or different inner surface structures, configurations or characteristics to ensure cooperative engagement of the plate. It would be well within the skill of a person trained in the art to create alternative devices and methods for maintaining the cooperative engagement of the plate with the drop, straight, oblique or other slots of the finger guard. FIG. 9B illustrates an example of this embodiment.

With this embodiment, the biosafety blade can be grasped in the fingers. Slight pressure applied to the finger guards can cause the sliding mechanisms 97 to move out of the drop slot. As the sliding mechanisms are pushed out of the drop slot, the front end of the plate contacts the blade surface and rotates the plate to be generally parallel with the blade. If necessary, one finger, typically the index finger, can be used to assist in moving the plate over the sharp edge. Continued pressure applied to the finger guards can be used to move the sliding mechanisms, thus the plate, towards the following face of the finger guards. This procedure can not only expose the sharp edge of the blade, but can also simultaneously bend the blade for use In a further embodiment, an oblique slot has one or more stop gaps 55 which a sliding mechanism 97 can engage with. A stop gap 55 can be similar to a stop 21 in an oblique cut-out 20, described above, in that the stop gap 55 can be engaged with a sliding mechanism 97 to hold a plate in a pre-determined position or curvature. Thus, as the blade is being squeezed to move the plate away from the sharp edge 14, the one or more sliding mechanisms can engage with a stop gap within the oblique cut-out to inhibit movement of the plate. Once the sliding mechanism is engaged with a stop gap, a constant pressure on the plate and blade can maintain the plate and blade in a particular curvature or position. In a further embodiment, the stop gap is shaped such that increased pressure, i.e., squeezing, of the blade ends causes the sliding mechanism to disengage with a stop gap and continue moving away from the sharp edge. In a still further embodiment, the shape of a stop gap is such that it will not inhibit the movement of the sliding mechanism, thus the plate, towards the sharp edge when pressure is not applied to the blade ends.

In one embodiment, a stop gap is generally a notch located within a slot. The notch can be very similar to a drop slot, in that it can be continuous with a slot and allow the sliding mechanism to move in and out as necessary when pressure is applied. In one embodiment, a notch has one or more angled and/or curved walls. In a further embodiment, a stop gap has a first wall 57 that is angled and/or curved sufficiently to temporarily inhibit motion of a sliding mechanism once engaged, an example of which is shown in FIG. 9B. The angle and/or curve of the first side can also be such that increased pressure applied to the sliding mechanism can force it to slide, roll, or otherwise move over the first side and back into the slot, so as to continue moving away from the sharp edge 14. In a further embodiment, a stop gap has a second wall 58 that is also angled and/or curved. In a still further embodiment, the second wall 58 has an angle and/or curve greater than the angle and/or curve of the first wall, such as shown, for example, in FIG. 9B. This can allow the second wall 58 to aid a sliding mechanism in engaging with the notch as it moves away from the sharp edge. However, the angle and/or curve of the second wall can be such that it also allows a sliding mechanism to move uninhibited towards the sharp edge 14 of a blade when pressure on the blade ends is reduced or eliminated. This can ensure that if the biosafety blade is not being held properly, the plate will automatically move towards and cover the sharp edge.

Figure 10A:
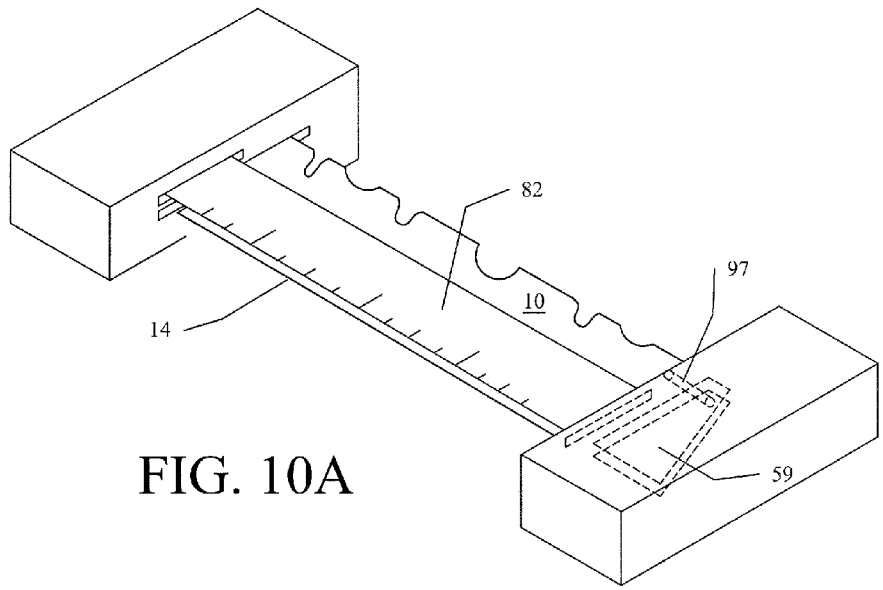
FIGS. 10A and 10B illustrate an embodiment wherein the plate is stationary and the blade itself can slide within one or more reverse oblique slots and move away from the one or more plates to expose the sharp edge.
Figure 10B:
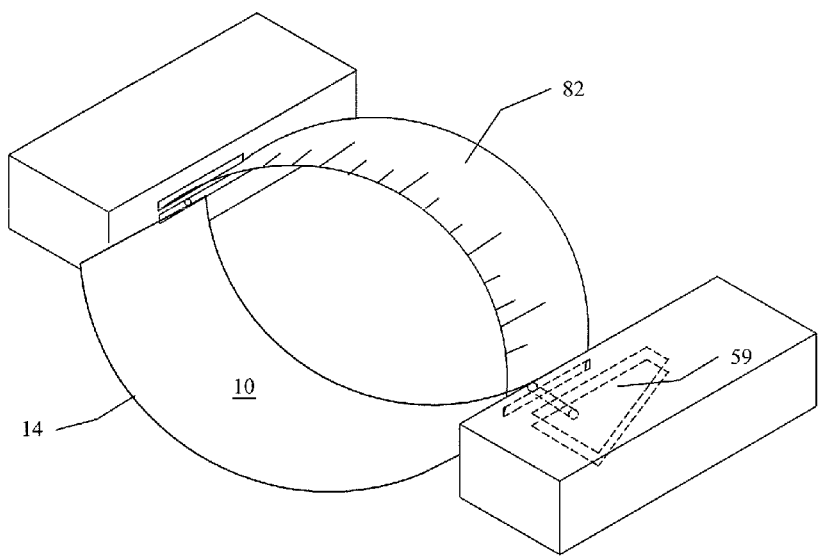

With minimal adjustment, the above-described embodiments could be utilized to cause the blade to move relative to the plate which may be straight, bent or curved as described above. In one another embodiment, one or more plates are secured within one or more slots in finger guards. The blade can be operatively engaged with a reverse oblique slot 59, the same as or similar to the methods described above. With this embodiment, the oblique slot can have an opposite orientation, where the slot is instead wider near the front face 50 of the finger guard. When the finger guards are squeezed, the plates remain in place, but the blade can move forward, towards the leading face 50, to expose the sharp edge. FIGS. 10A and 10B show an example of this embodiment. In FIG. 10A, it can be seen that the blade is protected by the overlaying plate. Additionally, two plates may be used above and below the blade similar to FIG. 7. In FIG. 10B, it can be seen that when the finger guards are brought closer together, the blade bends downward and slides forward in the oblique slot, while the plate remains stationary and bows upwards. Alternatively the plate may bow downwards as well.

The above-described embodiments herein have been described with the use of one or more plates that have a single construction, meaning they comprise for the most part at single unit. But alternative embodiments could be realized wherein the plate can comprise two or more sections with two or more plates or sliding mechanism ends. More specifically, the plate can be divided lengthwise (L) into two or more longitudinal sections. Conversely, the plate can be divided along its width (W). These sections can further be flexibly joined together to hold the sections in a coplanar, yet flexible fashion. Alternatively, the sections may not be coplanar and may act independently from one another. This flexible plate embodiment could be utilized advantageously with one or more of the herein described embodiments.

While many of the embodiments are described herein for use with a half-blade, these same devices and methods could be utilized with an intact or whole blade having either one or two sharp edges. For use with a double-edged blade, the components described herein can be utilized with each edge of the blade such that a double-edged blade would have the same biosafety blade components on each side.

Thus, in further embodiments, additional plate(s) similar to FIGS. 3F, 5C, 7, 9B and 10A could be attached between the finger guards at or about their following faces similar to FIG. 6A. With these embodiments, a single intact or whole blade or a double-edged blade would be protected on all sides and may be provided with additional support to the device The various components of the embodiments described herein can be packaged and sold separately. This can allow a user options for assembling a biosafety blade of the subject invention. Alternatively, the various components could be presented as parts of a kit that can be assembled as desired by a user. The kit can include blades or it can allow a user to assemble the components with their own blade. In still another embodiment, a biosafety blade can be pre-assembled with one or more of the components. This allows a user to obtain already prepared biosafety blades and eliminates most or all of the assembly process. The biosafety blade or its components may be sterilely packaged or capable of being sterilized via various means. The biosafety blade or its components may be disposable or reusable.

The embodiments of the invention described herein solve the problems inherent with utilizing safety razor blades, particularly for medical procedures. The embodiments described herein provide more comfortable and accurate ways to hold and manipulate a blade. The embodiments described herein also address the problem of unwanted and dangerous contact with the sharp edge of a blade by providing various devices for covering and securing a blade and preventing recoil and flying projectiles.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

I claim:

1. A biosafety blade device comprising:
   two finger guards, each comprising
      an outside face, and
      an inside face with at least two slots therein for engaging with a blade, such that in use with a blade engaged between the finger guards, the inside faces are generally facing each other;
   at least one blade guard disposed between the finger guards, wherein the blade guard comprises at least one plate having a first plate end and a second plate end, wherein each plate end is operably connected with one of the finger guard slots;
   such that a blade operably connected with a slot in each finger guard is positioned parallel to the plate so that the plate inhibits contact with the sharp edge of the blade, when the blade is not in use.

2. A biosafety blade device, according to claim 1, further comprising a blade having at least one sharp edge extending between two blunt ends, wherein each blunt end is engaged with a slot in one of the two finger guards, such that the blade guard inhibits contact with the sharp edge.

3. A biosafety blade device according to claim 2, wherein at least one of the blade and the blade guard is operably engaged with the slot by a resistance fit.

4. A biosafety blade device according to claim 2, wherein at least one of the blade and the blade guard is operably engaged with the slot by one or more securing structures.

5. A biosafety blade device according to claim 4, wherein the securing structure is an adhesive.

6. A biosafety blade device according to claim 4, wherein the securing structure is a rod secured within each of the slots that engage a plate end.

7. A biosafety blade device according to claim 1, wherein at least one of the finger guards and the blade guard further comprises measuring gradations.

8. A biosafety blade device according to claim 2, wherein each of the finger guards comprises a slot for receiving a plate end and a slot for receiving a blunt end of a blade.

9. A biosafety blade device according to claim 8, further comprising a tab piece operably connected to the plate such that it contacts the blade.

10. A biosafety blade device according to claim 9, further comprising a fin on the tab piece, such that the fin has an edge that contacts the blade.

11. A biosafety blade device according to claim 1, wherein the first and second plate ends are slidably engaged within the finger guard slots.

12. A biosafety blade device according to claim 9, further comprising one or more stop components within each of the slots that engage the plate ends.

13. A biosafety blade device according to claim 10, wherein the tab is operably connected proximal to the front edge of the plate such that it overlaps at least some portion of the blade.

14. A biosafety blade device according to claim 10, wherein the fin has a continuous edge in contact with the blade.

15. A biosafety blade device according to claim 10, wherein the fin has a notched, toothed, bristled, or otherwise discontinuous edge in contact with the blade.

16. A biosafety blade device according to claim 10, wherein the fin has a circular or semi-circular edge in contact with the blade with an apex portion that urges the blade to bend in a direction opposite to the plate.

17. A biosafety blade device, according to claim 16, wherein the tab exerts force against the blade so that the blade maintains a curved shape.

18. A biosafety blade device according to claim 13, wherein at least one of the finger guards and blade guard further comprises one or more locking structures.

19. A biosafety blade device according to claim 18, wherein the blade guard comprises one or more locking structures comprising one or more of raised ridges, dimples, ribs, pawls, cut-outs, notches, grooves, ducts, and swing-arm locks, such that the blade guard catches against or engages with a blade to lock the biosafety blade in place inhibiting contact with the sharp edge.

20. A biosafety blade device according to claim 10, wherein at least one of either of the finger guards and blade guard further comprises one or more locking structures.

21. A biosafety blade device according to claim 20, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

22. A biosafety blade device according to claim 1, further comprising one or more guides on the at least one plate.

23. A method of using a biosafety blade device according to claim 2, wherein the method comprises,
   grasping the biosafety blade with a finger placed against the outside face of each of the finger guards, and
   squeezing the outside face of the finger guards to bring the inside faces closer together, so as to cause the blade engaged with the finger guards to curve and the at least one blade guard to bow.

24. A method according to claim 23, wherein at least one of the blade and the blade guard is secured in the slot by a resistance fit.

25. A method according to claim 24, wherein at least one of the blade and the blade guard is secured in the slot by one or more securing structures.

26. A method according to claim 25, wherein the securing structure is an adhesive.

27. A method according to claim 25, wherein the securing structure is a rod secured within each of the slots that engage a plate end.

28. A method according to claim 23, wherein at least one of the finger guards and blade guard further comprises measuring gradations.

29. A method according to claim 23, wherein each of the finger guards comprises at least one slot for receiving a plate end and at least one other slot for receiving a blunt end of a blade.

30. A method according to claim 23, further comprising a tab piece operably connected to the plate so that it contacts the blade.

31. A method according to claim 30, further comprising a fin on the tab piece, such that the fin has an edge that contacts a blade.

32. A method according to claim 23, wherein the first and second plate ends are slidably operably engaged within the finger guard slots and wherein the method further comprises using a finger to slide the blade guard away from the sharp edge.

33. A method according to claim 32, further comprising one or more stop components within each of the slots that engage the plate ends.

34. A method according to claim 31, wherein the tab is operably connected to the proximal end of the plate, such that the tab overlaps at least some portion of the sharp edge of the blade.

35. A method according to claim 30, wherein the fin has a continuous edge in contact with the blade.

36. A method according to claim 30, wherein the fin has a notched, toothed, bristled, or otherwise discontinuous edge in contact with the blade.

37. A method according to claim 23, wherein the fin has a circular or semi-circular edge with an apex portion that urges the blade to bend in a direction opposite of the plate to which it is attached.

38. A method according to claim 37, wherein the tab and fin exert force against the blade so that the blade maintains a curved shape.

39. A method according to claim 34, wherein at least one of the finger guards and blade guard further comprises one or more locking structures.

40. A method according to claim 23, further comprising one or more guides on the at least one plate.

41. A biosafety blade device comprising:
a blade having at least one sharp edge extending between a first blunt end and a second blunt end;
two finger guards, each comprising,
an outside face, and
an inside face with at least three slots therein, wherein the inside faces of the finger guards generally face each other and the first blunt end and the second blunt end are operably connected with a slot in each of the finger guards,
a blade guard disposed between the finger guards, wherein the blade guard comprises,
two or more plates, each with a first plate end and a second plate end, wherein each plate end is operably engaged with one of the slots in a finger guard,
such that the two or more plates are positioned parallel to each other, with the blade between and parallel to the plates, so that the plates inhibit contact with the sharp edge when not in use.

42. A biosafety blade device according to claim 41, further comprising a cut-out in the blade that is generally parallel to the blunt ends.

43. A biosafety blade device according to claim 42, further comprising at least one coupling positioned within the at least one cut-out and fixedly attached to the two or more plates.

44. A biosafety blade device according to claim 41, wherein the plates slide simultaneously parallel to the blade.

45. A biosafety blade device according to claim 41, wherein at least one of the finger guards and blade guards further comprises measuring gradations.

46. A biosafety blade device according to claim 44, further comprising a tab piece operably connected to one of the at least two plates, so that it contacts the blade.

47. A biosafety blade device according to claim 46, further comprising a fin on the tab piece such that an edge of the fin contacts the blade.

48. A biosafety blade device according to claim 47, wherein the fin has a continuous edge in contact with the blade.

49. A biosafety blade device according to claim 47, wherein the fin has a notched, toothed, bristled or otherwise discontinuous edge in contact with the blade.

50. A biosafety blade device according to claim 49, wherein the fin has a circular or semi-circular edge in contact with the blade with an apex portion that urges the blade to bend in a direction opposite of the plate to which it is attached.

51. A biosafety blade device according to claim 49, wherein the tab is operably connected proximal to the front edge of the plate and overlaps at least some portion of the sharp edge of the blade.

52. A biosafety blade device according to claim 51, further comprising one or more stop components within one or more of the slots.

53. A biosafety blade device according to claim 51, wherein at least one of the finger guards and blade guard further comprises one or more locking structures.

54. A biosafety blade device according to claim 53, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

55. A biosafety blade device according to claim 50, wherein at least one of either of the finger guards and blade guard further comprises one or more locking structures.

56. A biosafety blade device according to claim 55, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

57. A biosafety blade device according to claim 51, wherein at least one of either of the finger guards and blade guard further comprises one or more locking structures.

58. A biosafety blade device according to claim 57, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

59. A biosafety blade device according to claim 41, further comprising one or more guides on either or both of the at least two plates.

60. A biosafety blade device according to claim 41, wherein at least one of the blade and the plates is operably engaged with the slot by a resistance fit.

61. A biosafety blade device according to claim 41, wherein at least one of the blade and the blade guards are operably engaged with the slot by one or more securing structures.

62. A biosafety blade device according to claim 61, wherein the securing structure is an adhesive.

63. A biosafety blade device according to claim 61, wherein the securing structure is a rod secured within a slot to which the one or more plate ends of the at least two plates is movably attached.

64. A method of using a biosafety blade device according to claim 41, the method comprising:
grasping the biosafety blade device with a finger placed against the outside face of each of the finger guards,
placing a finger against at least one of the plates and sliding the plate away from the sharp edge, and
squeezing the outside faces of the finger guards so as to bring the inside faces closer together, causing the blade to curve and the at least two plates to bow.

65. A method according to claim 64, wherein at least one of the blade and the blade guards is operably engaged with the slot by a resistance fit.

66. A method according to claim 64, wherein at least one of the blade and the blade guards is operably engaged with the slot by one or more securing structures.

67. A method according to claim 66, wherein the securing structure is an adhesive.

68. A method according to claim 66, wherein the securing structure is a rod secured within each of the slots that engage a plate end.

69. A method according to claim 64, wherein at least one of a finger guard and a plate comprises measuring gradations.

70. A method according to claim 64, further comprising a tab piece operably connected to at least one plate so that the tab piece contacts the blade.

71. A method according to claim 70, further comprising a fin on the tab piece such that the fin has an edge that contacts the blade.

72. A method according to claim 70, further comprising one or more stop components within each of the slots that engages a plate end.

73. A method according to claim 70, wherein the tab is operably connected proximal to the front edge of the plate and overlaps at least some portion of the sharp edge of the blade.

74. A method according to claim 71, wherein the fin has a continuous edge in contact with the blade.

75. A method according to claim 71, wherein the fin has a notched, toothed, bristled, or otherwise discontinuous edge in contact with the blade.

76. A method according to claim 71, wherein the fin has a circular or semi-circular edge with an apex portion that urges the blade to bend in a direction opposite of the plate to which it is attached.

77. A method according to claim 76, wherein the tab and fin exert force against the blade so that the blade maintains a curved shape.

78. A method according to claim 73, wherein at least one of the finger guards and blade guard further comprises one or more locking structures.

79. A method according to claim 78, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

80. A method according to claim 71, wherein at least one of the finger guards and blade guard further comprises one or more locking structures.

81. A method according to claim 80, wherein the one or more locking structures are on the blade guard and comprise at least one of raised ridges, dimples, ribs, pawls, cut-outs, notches, grooves, ducts, and swing-arm locks, such that the blade guard catches against or engages with a blade to lock the biosafety blade in place.

82. A method according to claim 64, further comprising one or more guides on at least one of the plates.

83. A biosafety blade device comprising:
two finger guards, each comprising,
an outside face, and
an inside face having a first slot that is an oblique slot and a second slot, such that in use with a blade having a sharp edge engaged between the finger guards, the inside faces are generally facing each other,
a blade guard disposed between the finger guards, wherein the blade guard comprises,
at least one plate with a first plate end and a second plate end, wherein each of the plate ends has an operable connection with the oblique slot in each finger guard, such that, when a blade is engaged between the finger guards, the plate is disposed generally perpendicular to and inhibits contact with the blade, wherein the at least one plate becomes parallel with the blade and moves away from the sharp edge when the two plate ends are brought closer together by squeezing the outside face of the finger guards.

84. A biosafety blade device, according to claim 83, further comprising a blade having at least one sharp edge extending between two blunt ends, wherein each blunt end is engaged with the second slot in each finger guard.

85. A biosafety blade device according to claim 83, further comprising a drop slot that is contiguous with the oblique slot in the one or more finger guards.

86. A biosafety blade device according to claim 85, wherein the at least one plate end has an operable connection with the drop slot in the at least one finger guard.

87. A biosafety blade device according to claim 86, wherein when the two plate ends are brought closer together, the operable connection of the plate ends is moved out of the drop slot and into the oblique slot.

88. A biosafety blade device according to claim 87, wherein the at least one plate has a longitudinal curve or bend.

89. A biosafety blade device according to claim 83, wherein at least one of the finger guards and the plate further comprises measuring gradations.

90. A biosafety blade device according to claim 83, further comprising a sliding mechanism at least one of the first plate end and the second plate end.

91. A biosafety blade device according to claim 90, wherein at least one of the sliding mechanism and the oblique slot is coated with polytetrafluoroethylene (PTFE).

92. A biosafety blade device according to claim 83, wherein the blade is operably engaged with the slot by a resistance fit.

93. A method of using a biosafety blade device according to claim 84, the method comprising, grasping the biosafety blade with a finger placed against the outside face of each of the finger guards, squeezing the outside faces of the finger guards so as to bring the inside faces closer together causing the at least one plate to rotate parallel to the blade, and wherein continued squeezing will cause the oblique slot to slide the at least one plate away from the sharp edge.

94. A method according to claim 93, wherein the biosafety blade further comprises a drop slot that is contiguous with the oblique slot.

95. A method according to claim 94, wherein the at least one plate end has an operable connection with the drop slot in the at least one finger guard.

96. A method according to claim 95, wherein squeezing the finger guards causes the operably engaged plate ends to move out of the drop slot and into the oblique slot.

97. A method according to claim 96, further comprising, placing a finger against the plate,
sliding the plate out of the drop slot and into the oblique slot before, or while simultaneously, squeezing the outside faces of the finger guards.

98. A method according to claim 93, wherein the at least one plate has a longitudinal curve or bend.

99. A method according to claim 93, wherein the blade is a separate component that is operably engaged with a slot in each finger guard.

100. A method according to claim 93, wherein at least one of the finger guards and plate further comprises measuring gradations.

101. A method according to claim 97, further comprising a sliding mechanism.

102. A method according to claim 101, wherein at least one of the sliding mechanism and the oblique slot is coated with polytetraflouroethylene (PTFE).

103. A biosafety blade device comprising:
a blade having at least one sharp edge and two blunt ends,
a blade guard comprising,
a plate having a first plate end and a second plate end;
one or more extensions that fixedly attach the first plate end and the second plate end proximal to two blunt ends,
such that the flat plate is longitudinally coplanar with the sharp edge so that when the blunt ends are squeezed together the flat plate and the blade bend.

104. A biosafety blade device according to claim 103, wherein the flat plate and the sharp edge are separated by a gap.

105. A biosafety blade device according to claim 103, wherein the at least one extension is configured so as to ensure that the blade and the blade guard bend in opposite directions when the blunt ends are squeezed together.

106. A biosafety blade device according to claim 104, wherein the gap is configured so as to ensure that the blade and the blade guard bend in opposite directions when the blunt ends are squeezed together.

107. A biosafety blade device according to claim 104, further comprising two or more finger guards, each comprising,
an outside face, and
an inside face with at least one slot therein, wherein the inside faces generally face each other and the blunt ends are operably connected with the at least one slot in each finger guard.

108. A biosafety blade device according to claim 107, wherein the at least one extension is configured to ensure that the blade and the blade guard bend in opposite directions when the blunt ends are squeezed together with the two or more finger guards.

109. A biosafety blade device according to claim 107, wherein the gap is configured so as to ensure that the blade and the blade guard bend in opposite directions when the blunt ends are squeezed together with the two or more finger guards.

110. A biosafety blade device according to claim 104, wherein the blade, the at least one blade guard, and the at least one extension are manufactured as a single unit.

* * * * *